(12) United States Patent
Klassen et al.

(10) Patent No.: US 9,119,850 B2
(45) Date of Patent: *Sep. 1, 2015

(54) COMPOSITIONS AND METHODS FOR WEIGHT LOSS IN AT RISK PATIENT POPULATIONS

(71) Applicant: Orexigen Therapeutics, Inc., La Jolla, CA (US)

(72) Inventors: Preston Klassen, La Jolla, CA (US); Kristin Taylor, San Diego, CA (US)

(73) Assignee: Orexigen Therapeutics, Inc., La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/635,518

(22) Filed: Mar. 2, 2015

(65) Prior Publication Data

US 2015/0182524 A1 Jul. 2, 2015

Related U.S. Application Data

(63) Continuation of application No. 14/322,810, filed on Jul. 2, 2014, now Pat. No. 8,969,371.

(60) Provisional application No. 61/913,216, filed on Dec. 6, 2013, provisional application No. 61/914,938, filed on Dec. 11, 2013, provisional application No. 61/984,580, filed on Apr. 25, 2014.

(51) Int. Cl.
*A61K 31/485* (2006.01)
*A61P 3/04* (2006.01)
*A61K 31/137* (2006.01)

(52) U.S. Cl.
CPC ............ *A61K 31/485* (2013.01); *A61K 31/137* (2013.01)

(58) Field of Classification Search
CPC ........................... A61K 31/137; A61K 31/485
See application file for complete search history.

(56) References Cited

U.S. PATENT DOCUMENTS

| | | | |
|---|---|---|---|
| 4,295,567 A | 10/1981 | Knudsen | |
| 4,828,836 A | 5/1989 | Elger et al. | |
| 5,403,595 A | 4/1995 | Kitchell et al. | |
| 5,486,362 A | 1/1996 | Kitchell et al. | |
| 5,512,593 A | 4/1996 | Dante | |
| 5,716,976 A | 2/1998 | Bernstein | |
| 5,817,665 A | 10/1998 | Dante | |
| 5,817,666 A | 10/1998 | Katz | |
| 5,948,799 A | 9/1999 | Cropp | |
| 5,958,962 A | 9/1999 | Cook | |
| 6,048,322 A | 4/2000 | Kushida | |
| 6,071,537 A | 6/2000 | Shank | |
| 6,071,918 A | 6/2000 | Cook | |
| 6,110,973 A | 8/2000 | Young | |
| 6,197,827 B1 | 3/2001 | Cary | |
| 6,210,716 B1 | 4/2001 | Chen et al. | |
| 6,306,436 B1 | 10/2001 | Chungi et al. | |
| 6,369,113 B2 | 4/2002 | Young | |
| 6,528,520 B2 | 3/2003 | Clemens | |
| 6,541,478 B1 | 4/2003 | O'Malley et al. | |
| 6,589,553 B2 | 7/2003 | Li et al. | |
| 6,995,169 B2 | 2/2006 | Chapleo et al. | |
| 7,109,198 B2 | 9/2006 | Gadde et al. | |
| 7,375,111 B2 | 5/2008 | Weber et al. | |
| 7,422,110 B2 | 9/2008 | Zanden et al. | |
| 7,462,626 B2 | 12/2008 | Weber et al. | |
| 7,682,633 B2 | 3/2010 | Matthews et al. | |
| 8,088,786 B2 | 1/2012 | McKinney et al. | |
| 8,318,788 B2 | 11/2012 | McKinney et al. | |
| 8,722,085 B2 | 5/2014 | McKinney et al. | |
| 8,815,889 B2 | 8/2014 | Cowley et al. | |
| 8,916,195 B2 | 12/2014 | McKinney et al. | |
| 2001/0025038 A1 | 9/2001 | Coffin et al. | |
| 2002/0025972 A1 | 2/2002 | Hintz | |
| 2002/0037836 A1 | 3/2002 | Henriksen | |
| 2002/0055512 A1 | 5/2002 | Marin et al. | |
| 2002/0198227 A1 | 12/2002 | Bernstein | |
| 2003/0068371 A1 | 4/2003 | Oshlack et al. | |
| 2003/0144271 A1 | 7/2003 | Shulman | |
| 2004/0005368 A1 | 1/2004 | Mann et al. | |
| 2004/0029941 A1 | 2/2004 | Jennings | |
| 2004/0204472 A1 | 10/2004 | Briggs et al. | |
| 2004/0242974 A1 | 12/2004 | Glover | |
| 2004/0254208 A1 | 12/2004 | Weber et al. | |
| 2005/0096311 A1 | 5/2005 | Suffin et al. | |
| 2005/0250838 A1 | 11/2005 | Challapalli et al. | |
| 2005/0277579 A1 | 12/2005 | Gadde et al. | |
| 2006/0058293 A1 | 3/2006 | Weber et al. | |
| 2006/0142290 A1 | 6/2006 | Weber et al. | |
| 2007/0099947 A1 | 5/2007 | Dean et al. | |
| 2007/0128298 A1 | 6/2007 | Cowley et al. | |
| 2007/0129283 A1 | 6/2007 | McKinney et al. | |

(Continued)

FOREIGN PATENT DOCUMENTS

| EP | 0 005 636 | 11/1979 |
|---|---|---|
| EP | 0 294 028 | 12/1988 |

(Continued)

OTHER PUBLICATIONS

A multicenter, randomized, double-blind, placebo-controlled study assessing the occurrence of major adverse cardiovascular events (MACE) in overweight and obese subjects with cardiovascular risk factors receiving naltrexone SR/bupropion SR, Adis Clinical Trials Insight (Nov. 15, 2011), 5 pp.

(Continued)

*Primary Examiner* — Savitha Rao
(74) *Attorney, Agent, or Firm* — Knobbe Martens Olson & Bear LLP

(57) ABSTRACT

The present disclosure relates to compositions, kits, uses, systems and methods related to naltrexone plus bupropion for treating an overweight or obese subject at increased risk of adverse cardiovascular outcomes. Preferably, the subject has had type-two diabetes for a period of less than 6 years or is a current smoker, optionally that does not have type-two diabetes.

3 Claims, 9 Drawing Sheets

(56) References Cited

U.S. PATENT DOCUMENTS

| | | |
|---|---|---|
| 2007/0149451 A1 | 6/2007 | Holmes |
| 2007/0270450 A1 | 11/2007 | Weber et al. |
| 2007/0275970 A1 | 11/2007 | Weber et al. |
| 2007/0281021 A1 | 12/2007 | McKinney et al. |
| 2008/0027487 A1 | 1/2008 | Patel et al. |
| 2008/0058407 A1 | 3/2008 | Baron et al. |
| 2008/0110792 A1 | 5/2008 | McKinney et al. |
| 2010/0166889 A1 | 7/2010 | Sanfilippo |
| 2010/0190793 A1 | 7/2010 | Weber et al. |
| 2011/0028505 A1 | 2/2011 | Mckinney et al. |
| 2011/0144145 A1 | 6/2011 | Tollefson |
| 2011/0172260 A1 | 7/2011 | Dunayevich et al. |
| 2012/0010232 A1 | 1/2012 | Weber et al. |
| 2013/0245055 A1 | 9/2013 | Wright |
| 2013/0252995 A1 | 9/2013 | Dunayevich et al. |
| 2014/0322318 A1 | 10/2014 | McKinney et al. |

FOREIGN PATENT DOCUMENTS

| | | |
|---|---|---|
| EP | 0 541 192 | 5/1993 |
| EP | 1 813 276 | 8/2007 |
| JP | 2003-509349 | 3/2003 |
| WO | WO 83/03197 | 9/1983 |
| WO | WO 96/09047 | 3/1996 |
| WO | WO 97/06786 | 2/1997 |
| WO | WO 97/41873 | 11/1997 |
| WO | WO 99/16375 | 4/1999 |
| WO | WO 99/38504 | 8/1999 |
| WO | WO 00/61139 | 10/2000 |
| WO | WO 01/52833 | 7/2001 |
| WO | WO 01/52851 | 7/2001 |
| WO | WO 01/58447 | 8/2001 |
| WO | WO 01/58451 | 8/2001 |
| WO | WO 02/24214 | 3/2002 |
| WO | WO 03/013524 | 2/2003 |
| WO | WO 03/013525 | 2/2003 |
| WO | WO 03/013479 | 3/2003 |
| WO | WO 03/097046 | 11/2003 |
| WO | WO 03/097051 | 11/2003 |
| WO | WO 2004/002463 | 1/2004 |
| WO | WO 2004/024096 | 3/2004 |
| WO | WO 2004/071423 | 8/2004 |
| WO | WO 2004/091593 | 10/2004 |
| WO | WO 2004/096201 | 11/2004 |
| WO | WO 2004/100992 | 11/2004 |
| WO | WO 2004/110375 | 12/2004 |
| WO | WO 2005/032555 | 4/2005 |
| WO | WO 2005/070461 | 8/2005 |
| WO | WO 2005/089486 | 9/2005 |
| WO | WO 2007/047351 | 4/2007 |
| WO | WO 2007/064586 | 6/2007 |
| WO | WO 2007/067341 | 6/2007 |
| WO | WO 2007/085637 | 8/2007 |
| WO | WO 2007/089318 | 8/2007 |
| WO | WO 2007/145863 | 12/2007 |
| WO | WO 2008/060963 | 5/2008 |
| WO | WO 2008/119978 | 10/2008 |
| WO | WO 2009/158114 | 12/2009 |
| WO | WO 2013/184837 | 12/2013 |

OTHER PUBLICATIONS

Adis Data Information BV, 2010, Naltrexone/Bupropion Contrave®, Naltrexone SR/Bupropion SR, Adis R&D Profile, 10(1):25-32.
Albaugh et al., 2005, Topiramate prevents the rapid weight gain and adiposity in a model of atypical antipsychotic drug-induced obesity, Fed. of American Soc. for Experimental Biology, 19(5, Suppl. S, Part 2):A1130.
Alger et al., Apr. 1991, Effect of a tricyclic antidepressant and opiate antagonist on binge-eating behavior in normoweight bulimic and obese, binge-eating subjects, The American Journal of Clinical Nutrition, 53(4):865-871.

Anderson et al., 2002, Bupropion SR enhances weight loss: a 48-week double-blind, placebo-controlled trial, Obesity R., 10(7):633-641.
Atlantis et al., Oct. 6, 2009, Obesity and depression or anxiety, BMJ 2009:339:B3868.
Bays et al., Aug. 1, 2007, Adiposopathy: treating pathogenic adipose tissue to reduce cardiovascular disease risk, Current Treatment Options in Cardiovascular Medicine, 9(4):259-271.
Bupropion (Oral Route), MayoClinic.com, 19 pp., 2009.
Campana et al., Jan. 2005, P.6.034 Naltrexone and cravings: does it work with eating disorders?, European Neuropsychopharmacology, 15:S283.
Carter et al. 2003. Pharmacologic treatment of binge-eating disorder, The International Journal of Eating Disorders, 34(Suppl):S74-S88.
Casado et al., Apr. 2003, Sibutramine decreases body weight gain and increases energy expenditure in obese Zucker rats without changes in NPY and orexins, Nutr Neurosci, 6(2):103-111 (abstract).
Chen et al., 2005, Combination treatment of clozapine and (No Suggestions) in resistant rapid-cycling bipolar disorder, Clin. Neuropharmacol. 28(3):136-138.
Chen et al., Jun. 2003, Nonketotic hyperosmolar syndrome from olanzapine, lithium, and valproic acid cotreatment, Annals of Pharmacotherapy, 37(6):919-920.
Ching, Mar. 1980, Influence of diphenylhydantoin upon oral glucose tolerance test in obesity, Chinese Medical Journal, 27(1):432-439.
Clark et al., 2003, Diabetes mellitus associated with atypical antipsychotic medications, Diabetes Technology & Therapeutics, 5(4):669-683.
ClinicalTrials.gov archive, May 2012, Cardiovascular outcomes study of Naltrexone SR/Bupropion SR in overweight and obese subjects with cardiovascular risk factors (the light study), 4 pp.
Cunningham, May 1963, Diethylpropion in the treatment of obesity, The Journal of the College of General Practitioner, 6(2):347-349.
Durgin et al., 2005, Pharmaceutical Practice for Technicians, 3rd Edition, Thomson Delmar Learning, p. 174.
Eckel et al., Apr. 16, 2005, The metabolic syndrome, The Lancet 365:1415-1428.
Esposito-Avella et al. (Jan. 1973) Studies on the protective effect of diphenylhyndantoin against alioxan diabetes in mice, Proceedings of the Society for Experimental Biology & Medicine, 142(1):82-85.
Fontela et al., Mar. 1986, Blocking effect of naloxone, dihydroergotamine and adrenalectomy in lithium-induced hyperglycaemia and glucose intolerance in the rat, Acta Endocrinologica, 111(3):342-348 (abstract).
Fulghesu et al. (Aug. 1993) Long-term naltrexone treatment reduces the exaggerated insulin secretion in patients with polycystic ovary disease, Obstetrics & Gynecology, 82(2):191-197.
Fuller et al. (1989) Fluoxetine: A Serotonergic Appetite Suppressant Drug, Drug Development Research, 17(1):1-15.
Gadde et al. "Bupropion for Weight Loss: An Investigation of Efficacy and Tolerability in Overweight and Obese Women" Obesity Research 9 (9): 544-551 (2001).
Gerich et al. (1972) In vitro inhibition of pancreative glucagon secretion by diphenylhydantoin, Journal of Clinical Endocrinology and Metabolism 35(6):823-824.
Gerra et al., Sep. 30, 2006, Effects of olanzapine on aggressiveness in heroin dependent patients, Progress in Neuro-Psychopharmacology & Biological Psychiatry, 30(7):1291-1298.
Givens et al. (1987) Reduction of hyperinsulinemia and insulin resistance by opiate receptor blockade in the polycystic ovary syndrome with acanthosis nigricans, Journal of Clinical Endocrinology and Metabolism, 64(2):377-382.
Goldstein et al. (Mar. 1994) Fluoxetine: a randomized clinical trial in the treatment of obesity, International Journal of Obesity and Related Metabolic Disorders, 17(3):129-135, CAS accession #9424430.
Greenway et al., Dec. 2009, Comparison of combined bupropion and naltrexone therapy for obesity with monotherapy and placebo, J. Clin Endocrinol Metab, 94(12):4898-4906.
Greenway et al., Jan. 2009, Rational design of a combination medication for the treatment of obesity, Obesity, 17(1):30-39.
Greenway et al., Jun. 2006, Bupropion and naltrexone for the treatment of obesity, Diabetes: Abstract Book: 66th Scientific Sessions, 55(Supplement 1):A395.

(56) References Cited

OTHER PUBLICATIONS

Greenway et al., Oct. 22, 2010, Effect of naltrexone plus bupropion on weight loss in overweight and obese adults (COR-I): a multicentre, randomized, double-blind, placebo-controlled, phase 3 trial, Lancet, 376:595-605.

Grunenthal, Neo-Eunomin Gebrauschsinformation, Neunomin Prescription Information, Feb. 2004, pp. 1-2.

Hagan et al., Dec. 1997, Combined naloxone and fluoxetine on deprivation-induced binge eating of palatable foods in rats, Pharmacol Biochem Behav, 58(4):1103-1107.

Halpern et al., Jul. 27, 2010, Combinations of drugs in the treatment of obesity, Pharmaceuticals, 3:2398-2415.

Hausenloy, 2009, Contrave™: Novel treatment for obesity, Future Lipidology, 4(3):279-285.

Home et al., Jul. 1988, Treatment of bulimia with bupropion: a multicenter controlled trial, The Journal of Clinical Psychiatry, 49(7):262-266.

Insulin Resistance and Pre-diabetes, http://diabetes.niddk.hih.gov/DM/pubs/insulineresistance/, NIH Publication No. 09/4893, Oct. 2008, 9 pp.

Islam et al., 1994, Naltrexone, Serotonin Receptor Subtype Antagonists, and Carbohydrate Intake in Rats, Pharmacology Biochemistry and Behavior, 48(1):193-201.

Janssen et al., 1999, Effects of sex on the change in visceral, subcutaneous adipose tissue and skeletal muscle in response to weight loss, International Journal of Obesity, 23, pp. 1035-1046.

Johnson et al., Oct. 14, 2010, Food effects on the pharmacokinetics of morphine sulfate and naltrexone hydrochloride extended release capsules, Advances in Therapy, 27(11):846-858.

Jonas et al.., 1986, Treatment of binge-eating an open-study of naltrexone, Society for Neuroscience Abstracts, 12(1):595.

Jones et al., 2003, Effect of naltrexone on food intake and body weight in Syrian hamsters depends on metabolic status, Physiology & Behavior 28:67-72.

Kelly et al., 2006, Adjunct divalproex or lithium to clozapine in treatment-resistant schizophrenia, Psychiatric Quarterly, 77(1):81-94.

Kennett et al., Nov. 2010, New approaches to the pharmacological treatment of obesity: can they break through the efficacy barrier?, Pharmacology Biochemistry and Behavior, 97(1):63-83.

Khaylis et al., Nov. 2010, A review of efficacious technology-based weight-loss interventions: five key components, Telemedicine and e-Health, 16(9):931-938.

Klein et al., Jun. 1, 2009, Naltrexone plus bupropion combination causes significant weight loss without worsening psychiatric symptoms, Diabetes, 58(Suppl. 1):A444.

Kristeller et al., Jan. 12, 1999, An exploratory study of a meditation-based intervention for binge eating disorder, J. Health Psychol, 4(3):357-363.

Kuk et al., 2006, Visceral fat is an independent predictor of all-cause mortality in men, Obesity, 14(2):336-341.

Lowry, Feb. 2008, Study: bupropion-naltrexone combo best for weight loss, Clinical Psychiatric News, 1 pp.

Luppino et al., Mar. 2010, Overweight, obesity, and depression: a systematic review and meta-analysis of longitudinal studies, Arch Gen Psychiatry, 67(3):220-229.

Marrazzi et al., Feb. 1995, Binge eating disorder: response to naltrexone, International Journal of Obesity, 19(2):143-145.

McElroy et al., Jun. 1, 2010, An open-label study evaluating the naltrexone SR/bupropion SR combination therapy in overweight or obese subjects with major depression, Diabetes, 59(Suppl. 1):A483.

McLaughlin et al., 1983, Nalmefene decreases meal size, food and water intake and weight gain in Zucker rats, Pharmacology Biochemistry and Behavior, 19(2):235-240 (abstract).

Midha et al., May 2005, Exposure measures applied to the bioequivalence of two sustained release formulations of bupropion, International Journal of Clinical Pharmacology and Therapeutics, 43(5):244-254.

Mills, et al., "Cardiovascular Events Associated with Smoking Cessation Pharmacotherapies: A Network Meta-Analysis," Circulation, 2014; 129:28-41.

Najim et al., Dec. 1, 1993, Role of endorphins in benzodiazepine-induced hyperglycaemia in mice, Pharmacology Biochemistry and Behavior, 46(4):995-997.

Naltrexone (Oral Route), MayoClinic.com, 11 pp., 2009.

National Institutes of Health, Apr. 18, 2008, Efficacy and safety study of combination therapy to treat uncomplicated obesity, http://clinicaltrials.gov/show/NCT00364871, 5 pp.

NDA 20-711, Approval Letter of Application No. NDA 20-711, Department of Health and Human Services, May 14, 1997, 4 pp.

Neumeister et al. 1999. Addition of naltrexone to fluoxetine in the treatment of binge eating disorder. Am. J. Psychiatry, 156(5):797.

Novi et al. (Apr.-Jun. 1990) The role of opioid antagonists in the treatment of obesity. Results of a clinical trial with naltrexone, Minerva Endocrinol. 15(2):121-123, Abstract.

O'Byrne et al., Jan. 1, 1990, Effects of drugs on glucose tolerance in non-insulin-dependent diabetes (part II), Drugs, Adis International Ltd., 40(2):204-219.

Olszewski et al. (Jun. 13, 2001) Evidence of Interactions Between Melanocortin and Opioid Systems in Regulation of Feeding, NeuroReport, 12(8):1727-1730.

Orexigen Therapeutics, Inc., A safety and efficacy study comparing naltrexone SR/bupropion SR and placebo in obese type 2 diabetics, http://clinicaltrials.gov/ct2/show/NCT00474630, 4 pp.

Orexigen Therapeutics, Inc., Method-of-use study assessing the effect of naltrexone sustained release (SR)/bupropion SR on body weight and cardiovascular risk factors in overweight and obese subjects, http://clinicaltrials.gov/ct2/show/NCT01764386, 5 pp. Feb. 9, 2013.

Ortho-Novum Tablets and Modicon Tablets Prescribing Information, Apr. 2002, 8 pp.

Otake et al. (May 15, 2005) Association of visceral fat accumulation and plasma adiponectin and colorectal ademona: evidence for participation of insulin resistance, Clinical Cancer Research 11:3642-3646.

Padwal, Oct. 6, 2009, Contrave, a bupropion and naltrexone combination therapy for the potential treatment of obesity, Curr. Opin. Investig. Drugs, 10(10):1117-1125 (abstract).

Paile-Hyvarinen et al., Mar. 14, 2003, Quality of life and metabolic status in mildly depressed women with type 2 diabetes treated with paroxetine: a single blind randomised placebo controlled trial, BMC Family Practice, Biomed Central, 4(1), 6 pp.

Pandit, 2007, Introduction to the Pharmaceutical Sciences, 1st Ed., Lippincott Williams & Wilkins, Baltimore, MD, p. 154.

Rao et al. (1998) Fixed-does combination therapy: panacea or poison?, Intensive Care Med, 24:283-285.

Reents et al. (1988) Nalozone and naltrexone, Chest, 93(1):217-219.

Scheen et al., May 1, 2005, Diabete sucre iatrogene: l'exemple des anti-phsychogiques atypiques, Revue Medicale de Liege, 60(5-6):455-460.

Schimmel et al., 1974, Inhibition by diphenylhydantoin of the diabetogenic action of streptozocin, Horm. Metab. Res. 6:475-477.

Sneer et al., Protective effect of diphenylhydantoin on the diabetes-inducing effect of alioxan, database accession No. 1980:34024.

Spigset et al. (2001) Therapeutic Approaches to Bulimia Nervosa, Expert Opinion on Therapeutic Patents, 11(3):463-477.

Tavakoli et al., Jul. 2003, Diabetic ketoacidosis in a patient with olanzapine, valproic acid, and venlafaxine, Southern Medical Journal, 96(7):729-730.

Turnbull et al., Jan. 1985, The effect of valproate on blood metabolite concentrations in spontaneously diabetic, ketoacidotic, bb/e wistar rats, Diabetes Research 2(1):45-48.

Van Gaal et al., Aug. 1998, Sibutramine and fat distribution: is there a role for pharmacotherapy in abdominal/visceral fat reduction?, Int J Obes Relat Metab Disord, Suppl 1:S38-40; discussion S41-2 (abstract).

Wadden et al., Jan. 2011, Weight loss with naltrexone SR/bupropion SR combination therapy as an adjunct to behavior modification: the COR-BMOD trial, Obesity, 19(1):110-120.

(56) References Cited

OTHER PUBLICATIONS

Werneke et al. (2002) Options for Pharmacological Management of Obesity in patients Treated with Atypical Antipsychotics, International Clinical Psychopharmacology, 17(4):145-160.
Wieczorek et al., 2001, The effects of the selective serotonin reuptake-inhibitor fluvoxamine on body weight in Zucker rats are mediated by cortocotrophin-releasing hormone, International Journal of Obesity, 25(10):1566-1569.
Wilcox et al., 2009, An open-label study of naltrexone and bupropion combination therapy for smoking cessation in overweight and obese subjects, Addictive Behaviors, 35(3):229-234.
Wolff (1995) Burger's Medicinal Chemistry and Drug Discovery, John Wiley & Sons, 5th Ed. 1:975-977.
Yeomans et al. (2002) Opioid peptides and the control of human ingestive behaviour, Neuroscience and Biobehavioral Reviews, 26:712-728.
Yu et al. (2005) Influence of insulin treatment on insulin sensitivity in insulin requiring type 2 diabetes patents, Diabetes Research and Clinical Practice, 68S1:S54-S59.
Zhu et al. (Apr. 3, 2002) Pharmacologic Treatment of Eating Disorders, Canadian Journal of Psychiatry, 47(3):227-234.
Zonisamide (Oral Route), MayoClinic.com, 12 pp., 2009.
International Search Report and Written Opinion dated Oct. 29, 2013 in PCT/US13/44368.
Altomonte et al., 1988, Effect of fenfluramine on insulin/growth hormone ratio in obese subjects, Pharmacology, 36(2):106-111.
Bakris et al., 2002, Orlistat improves blood pressure and control in obese subjects with treated but inadequately controlled hypertension, Journal of Hypertension, 20(11):2257-2267.
Bengtsson, 1993, The consequences of growth hormone deficiency in adults, Acta Endocrinol. (Copenh.), 128(Suppl 2):2-5.
Brown et al., 2012, Current and emerging directions in the treatment of eating disorders, Substance Abuse: Research and Treatment, 6:33-61.
Brunk, Sep. 1, 2009, Significant weight loss shown with naltrexone/bupropion combo, Thoracic Surgery News, http://www.thoracicsurgerynews.com/?id=95937&tx__ttnews[tt__news]=86987&cHash=a97b7f3c0f6a8c6a3b3ca96df9a6b73f, 1 pp.
Carson et al., May 1996, Pilot study of the use of naltrexone to treat the severe pruritis of cholestatic liver disease, Amer. J. Gastroenterology, 91(5):1022-1023.
Chakraborty et al., 2010, Management of anorexia and bulimia nervosa: an evidence-based review, Indian J Psychiatry, 52:174-186.
Clinical Trials.gov, A Multicenter, randomized, double-blind, placebo-controlled study assessing the occurrence of major adverse cardiovascular events (MACE) such as cardiovascular death, non-fatal myocardial infarction, and non-fatal stroke in overweight and obese subjects who are at a higher risk of having these events because they ahv diabetes and/or other cardiovascular risk factors, NTC01601704, May 7, 2013, 4 pp.
Clinical Trials.gov, Jul. 13, 2009, An open-label study assessing the safety and efficacy of naltrexone sustained release (SR)/bupropion sustained release (SR) in overweight or obese subjects with major depression, 2 pp.
ClinicalTrials.gov archive, Apr. 21, 2008, A phase 3 study comparing the safety and efficacy of naltrexone sr/bupropion sr and placebo in obese subjects with type 2 diabetes mellitus, 3 pp.
Croft et al. (Apr. 2002) Effect on body weight of bupropion sustained-release in patients with major depression treated for 52 weeks, Clinical Therapeutics 24(4):662-672.
Das et al., 2003, Controlled-release of oral dosage forms, Formulation, Fill & Finish, pp. 10-16.
De Boer et al., 1995, Clinical aspects of growth hormone deficiency in adults, Endocrine Reviews, 16(1):63-86.
Eid et al., 2005, Effective treatment of polycystic ovarian syndrome with roux-en-y gastric bypass, Surgery for Obesity and Related Diseases, 1:77-80.
Fujioka et al., Jan. 1987, Contribution of intra-abdominal fat accumulation to the impairment of glucose and lipid metabolism in human obesity, Metabolism, 36(1):54-59.
Ghisoli et al., 1980, Effects of dopaminergic receptor stimulation and opioid receptor blockade on GH incretion: preliminary findings, Boll. Soc. Ital. Biol. Sper., 56(12):1222-1225.
Ghisoli et al., 1980, Effects of interaction between 2-Br-α-ergocryptine (CB 154) and naloxone on the control of insulin secretion in normal man, Boll. Soc. Ital. Biol. Sper., 56(12):1215-1221.
Glod et al., Jul.-Sep. 2003, Open trial of bupropion sr in adolescent major depression, J Child Adolesc Psychiatr Nurs, 16(3):123-130.
Goodman & Gillman's, The Pharmacological Basis of Therapeutics, 19th Ed., Edited by J. Hardman and L. Limbird, 2001, p. 6.
Gormally et al., 1982, The assessment of binge eating severity among obese persons, Addict Behav, 7(1):47-55.
Gudmundur et al., 1997, Growth hormone treatment of abdominally obese men reduces abdominal fat mass, improves glucose and lipoprotein metabolism, and reduces diastolic blood pressure, J. Clin. Endocrin. and Metab., 82(3):727-734.
Guidance for Industry Estimating the Maximum Safe Starting Dose in Initial Clinical Trials for Therapeutics in Adult Healthy Volunteers, U.S. Department of Health and Human Services, U.S. Food and Drug Administration Center for Drug Evaluation and Research (CDER), Pharmacology and Toxicology, Jul. 2005.
Herper, Mar. 5, 2015, Top FDA Official Says Orexigen Study Result 'Unreliable,' Misleading, http://www/forbes.com/sites/matthewherper/, 4 pp.
Hollander et al., Oct. 21, 2013, Effects of naltrexone sustained-release/bupropion sustained release combination therapy on body weight and glycemic parameters in overweight and obese patients with type 2 diabetes, Diabetes Care, 36(12):4022-4029.
Husten, Mar. 3, 2015, Orexigen Released Interim Data Without Approval of Trial Leaders, http://ww/forbes.com/sites/harryhusten, 6 pp.
Ioannides-Demos et al., 2005, Pharmacotherapy for obesity, Drugs, 65(10):1391-1418.
Jain et al. (Oct. 2002) Bupropion SR vs. Placebo for Weight Loss in Obese Patients with Depressive Symptoms, Obesity Research, 10:1049-56.
Kivimaki et al., Common mental disorder and obesity—insight from four repeat measures over 19 years: prospective Whitehall II cohort study, BMJ 2009; 339:b3765.
Laessle et al., May 1997, A comparison of resting metabolic rate, self-rated food intake, growth hormone, and insulin levels in obese and nonobese preadolescents, Physiol. Behav., 61(5):725-729.
Ludman et al., "Does depression reduce the effectiveness of behavioral weight loss treatment?" Behav Med. 2010; 35(4):126-134 (abstract).
Malhotra et al. (2002) Medical Management of Obesity Associated With Mental Disorders, Journal of Clinical Psychiatry, 63(suppl 4):24-32.
McElroy et al., Jun. 2013, Naltrexone/bupropion combination therapy in overweight or obese patients with major depressive disorder: results of a pilot study, Prim Care Companion CNS Disord, 15(3), 17 pp.
McElroy et al., May 7, 2012, Pharmacological management of binge-eating disorder: current and emerging treatment options, Therapeutics and Clinical Risk Management, 8:219-241.
Meyer et al., Sep. 1984, Bioequivalence, dose-proportionality, and pharmacokinetics of naltrexone after oral administration, J. Clin. Psychiatry, 45(9)(Sec. 2):15-19.
Milano et al., May-Jun. 2005, Treatment of bulimia nervosa with fluvoxamine: a randomized controlled trial, Advances in Therapy, 22(3):278-283.
Oncken et al., 2001, Adverse effects of Oral naltrexone: an analysis of data from two clinical trials, Psychopharmacology, 154:397-402.
Pagoto et al., Association of Major Depression and Binge Eating Disorder with Weight Loss in a Clinical Setting, Obesity, Nov. 2007; 15(11):2557-2559.
Patel et al., Jun. 2011, A hospital-based observational study of type 2 diabetic subjects from Gujarat, India, Journal of Health, Population and Nutrition, 29(3):265-272.
Pearlstein et al., 2003, A double-blind, placebo-controlled trial of fluvoxamine in binge eating disorder; a high placebo response, Arch Womens Ment Health, 6:147-151.

(56) References Cited

OTHER PUBLICATIONS

Plodkowski et al., 2009, Bupropion and naltrexone: a review of their use individually and in combination for the treatment of obesity, Expert Opin. Pharmacother. 10(6):1069-1081.

Ramlo-Halsted et al., 2000, The natural history of type 2 diabetes: practical points to consider in developing prevention and treatment strategies, Clin. Diabetes, 18(2).

Rao, Mar. 2001, Insulin resistance syndrome, American Family Physician, 63(6):1159-1163.

Remington's Pharmaceutical Sciences, 1980, 16th ed., Mack Publishing Company, Arthur Osol. Editor, pp. 1553-1594.

Remington's Pharmaceutical Sciences, 1980, 16th ed., Mack Publishing Company, Arthur Osol. Editor, pp. 1592-1597.

Ricca et al., 2001, Fluoxetine and fluvoxamine combined with individaul congitive-behavior therapy in binge-eating disorder: a one-year follow-up study, Psychotherapy and Psychosomatics, 70:298-306.

Richelsen et al., Feb. 1994, Growth hormone treatment of obese women for 5 wk: effect on body composition and adipose tissue LPL activity, Am J. Physiol., 266(2 Pt 1):11-16.

Shuman et al., Jun. 1986, Abnormal body fat distribution detected by computed tomography in diabetic men, Investigative Radiology, 21(6):483-487.

Stansfeld et al., Aug. 1992, Social class and minor psychiatric disorder in British civil servants: a validated screening survey using the General Health Questionnaire, Psychological Medicine, 22:739-749.

Stedman's Medical Dictionary, 28th ed., Lippincott Williams & Wilkins, Philadelphia, 1999, pp. 490-491 and 1552.

Tallarida, 2001, Drug synergism: its detection and applications, J. Pharmacol. and Expt. Therap., 298(3):865-872.

Wellbutrin® (bupropion hydrochloride) tablets, in Physicians' Desk Reference, 49th edition, 1995, pp. 824-827, 150.

White et al., 2003, Clarifying the role of insulin in type 2 diabetes management, Clinical Diabetes, 21(1):14-21.

Wong et al., Aug. 2004, Starting insulin treatment in type 2 diabetes, Australian Prescriber, 27(4):93-96.

Cleveland Clinic Press Release: "Clinical Trial Testing Safety of Obesity Drug Contrave Halted; 50 Percent Interim Data Released by the Study's Executive Committee", May 12, 2015, retrieved from http://my.clevelandclinic.org/about-cleveland-clinic/newsroom/releases-videos-newsletters/2015-5-12-clinical-trial-testing-safety-of-obesity-drug-contrave-halted.

Orexigen Therapeutics Press Release: "Orexigen Therapeutics Provides Statement on Termination of the Light Study and Updates on Contrave Collaboration with Takeda Pharmaceuticals", May 12, 2015, retrieved from http://ir.orexigen.com/phoenix.zhtml?c=207034&p=irol-newsArticle_Print&ID=2047312.

Orexigen Therapeutics Press Release: "Takeda Pharmaceuticals and Orexigen Therapeutics Announce Termination of the Cardiovascular Outcomes Study (Light Study) of the Obesity Drug Contrave® (naltrexone HCI and bupropion HCI)", May 12, 2015, retrieved from http://ir.orexigen.com/phoenix.zhtml?c=207034&p=irol-newsArticle_Print&ID=2046959.

Herper, "Heart Benefit for Orexigen Drug Nearly Vanishes with New Data", Forbes, May 12, 2015, retrived from http://www.forbes.com/sites/matthewherper/2015/05/12/heart-benefit-for-orexigien-drug-nearly-vanishes-with-new-data/.

Herper, "A Top Cardiologist Says a Diet Drug Maker Misled Patients and Investors", Forbes, May 12, 2015, retrieved from http://www.forbes.com/sites/matthewherper/2015/05/12/a-top-cardiologist-says-a-diet-drug-maker-misled-patients-and-investors/#.

Mukherjee, "Update: Takeda threatens to break off Orexigen collab after Contrave data drama", BioPharmaDive, May 12, 2015, retrieved from http://www.biopharmadive.com/news/update-takeda-threatens-to-break-off-orexigen-collab-after-contrave-data-d/396940/.

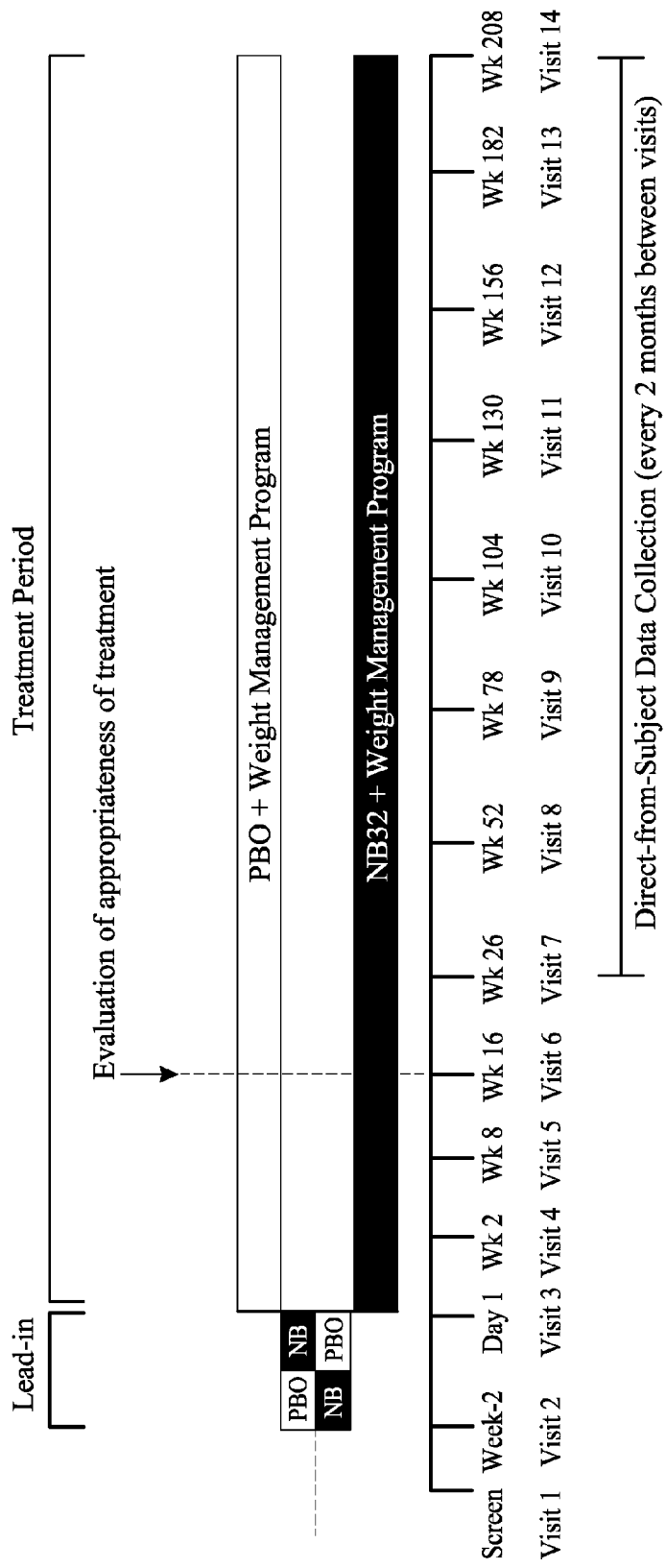
Figure 1. Study Design

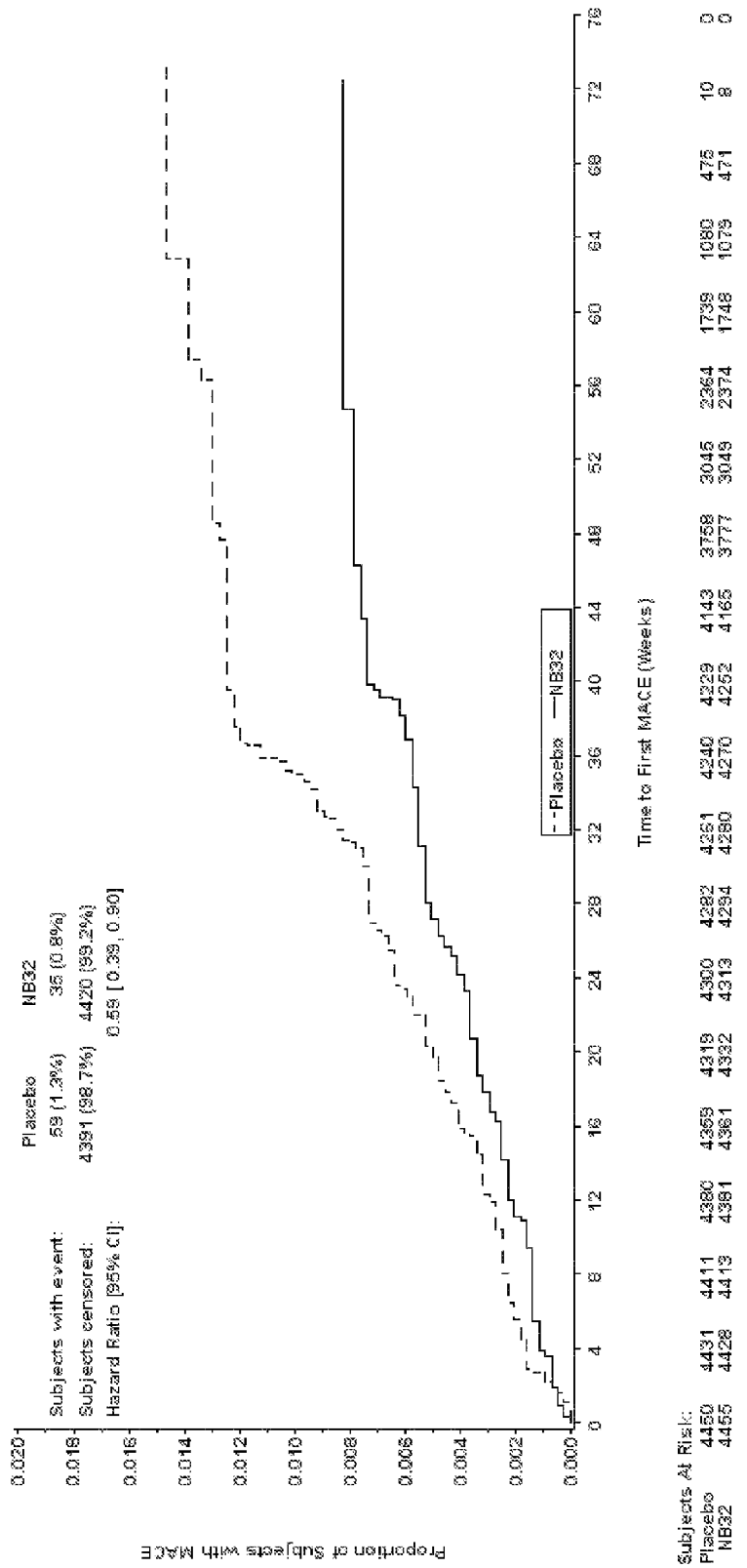

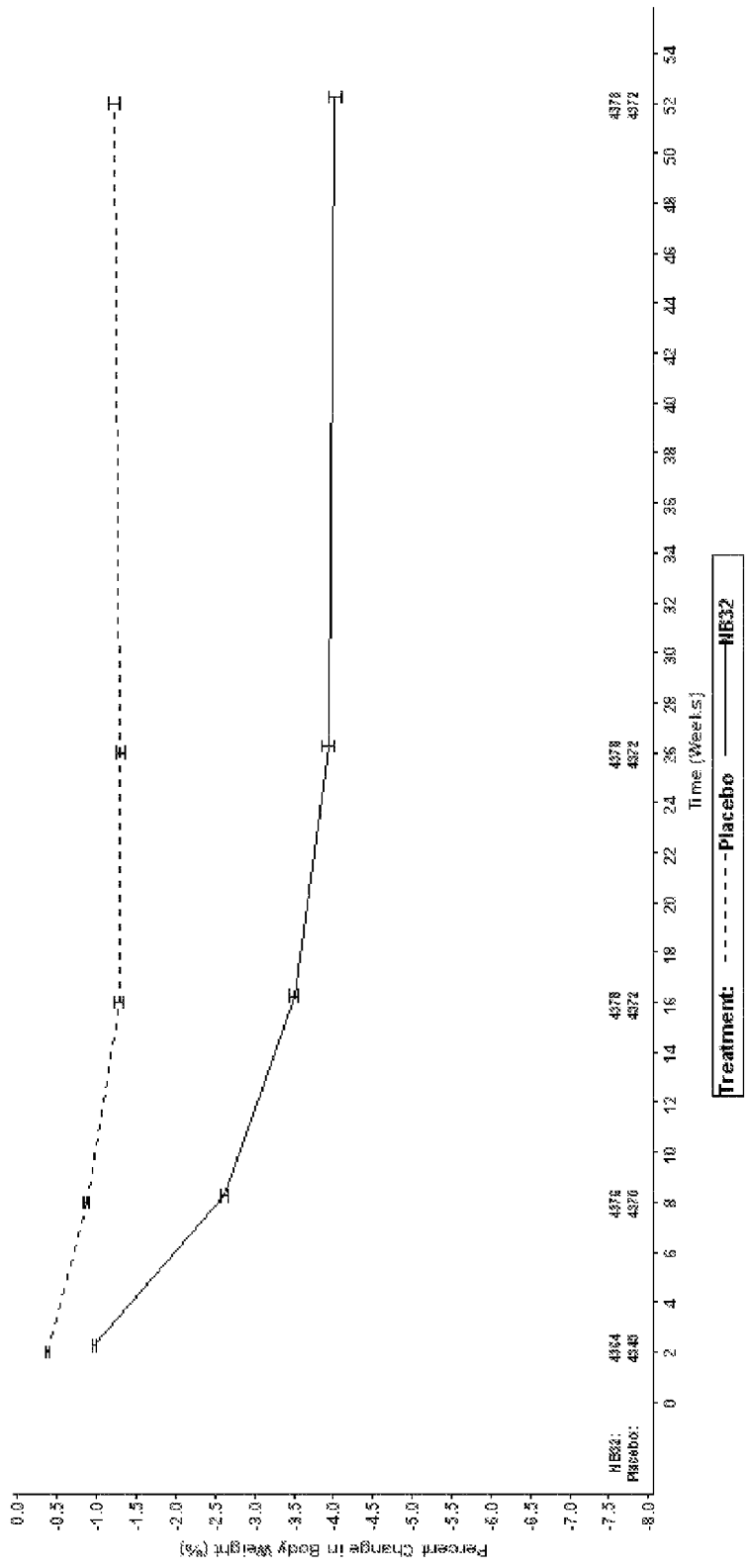

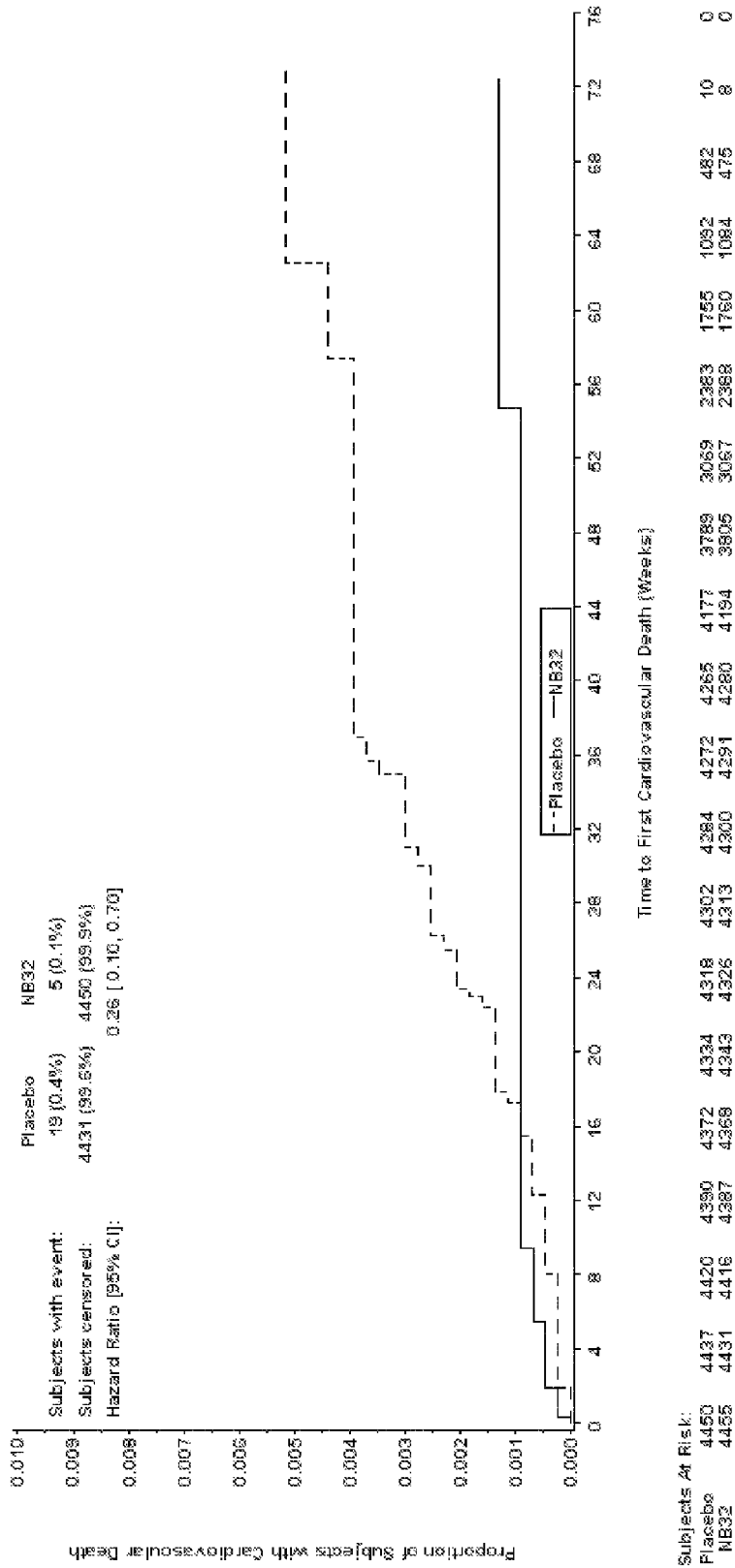

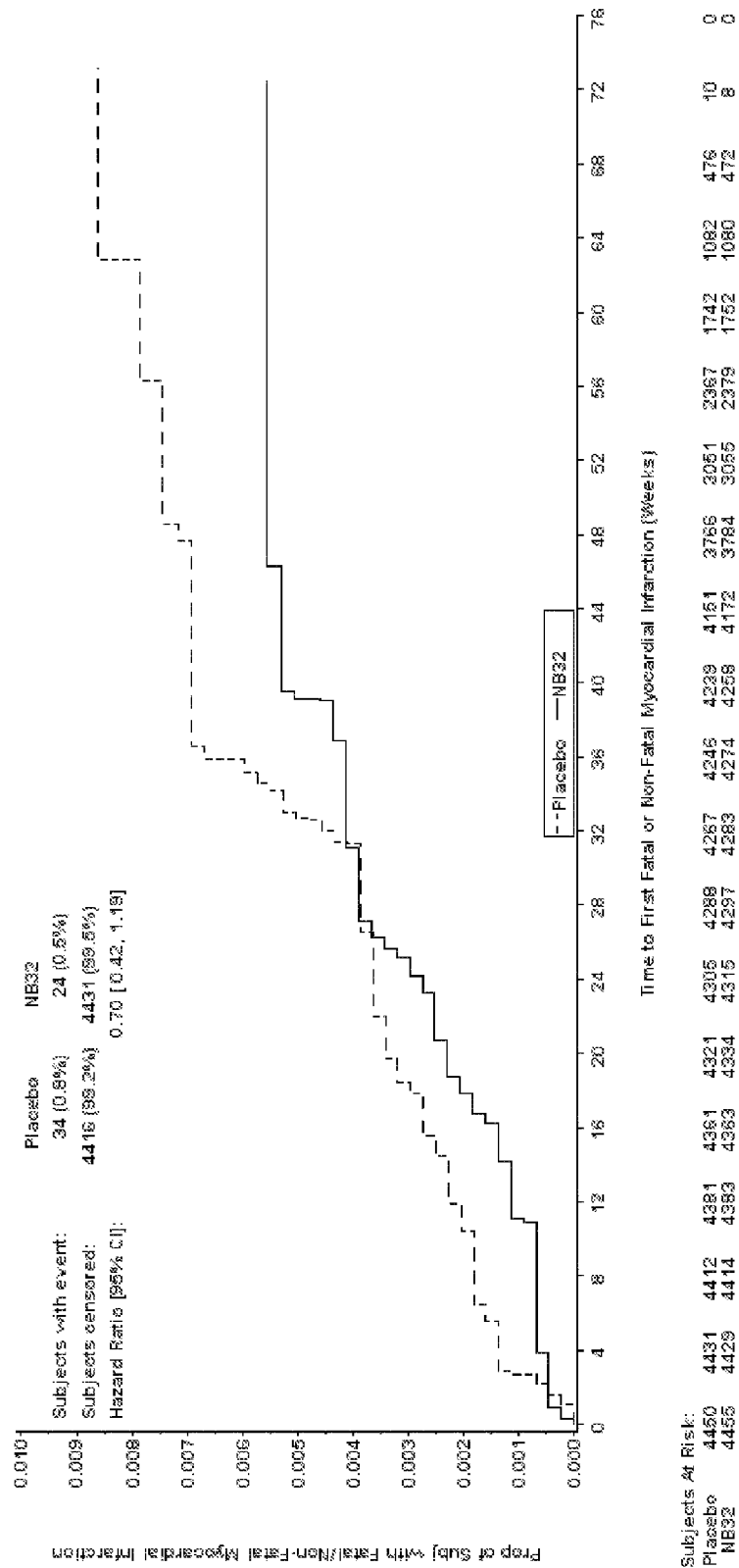

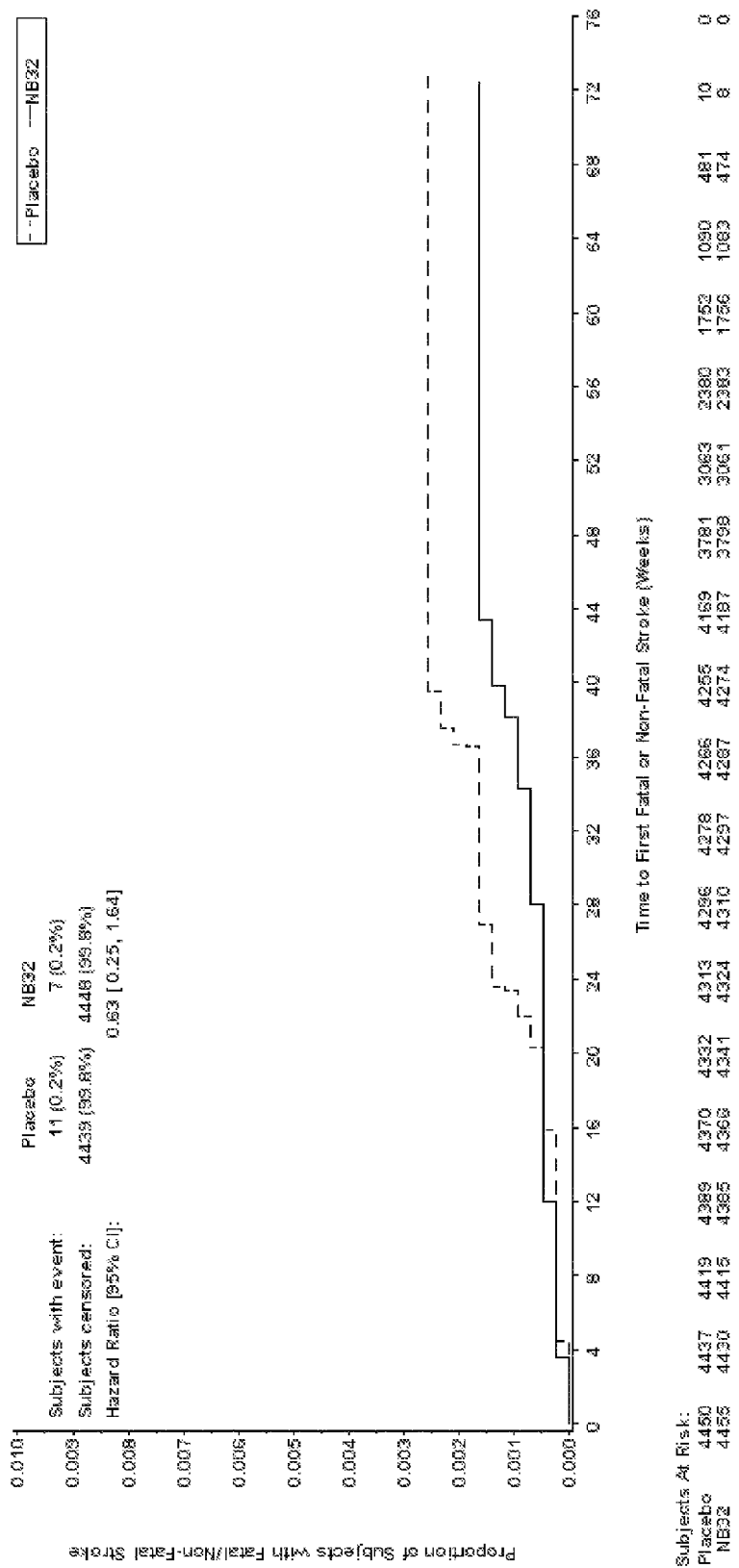

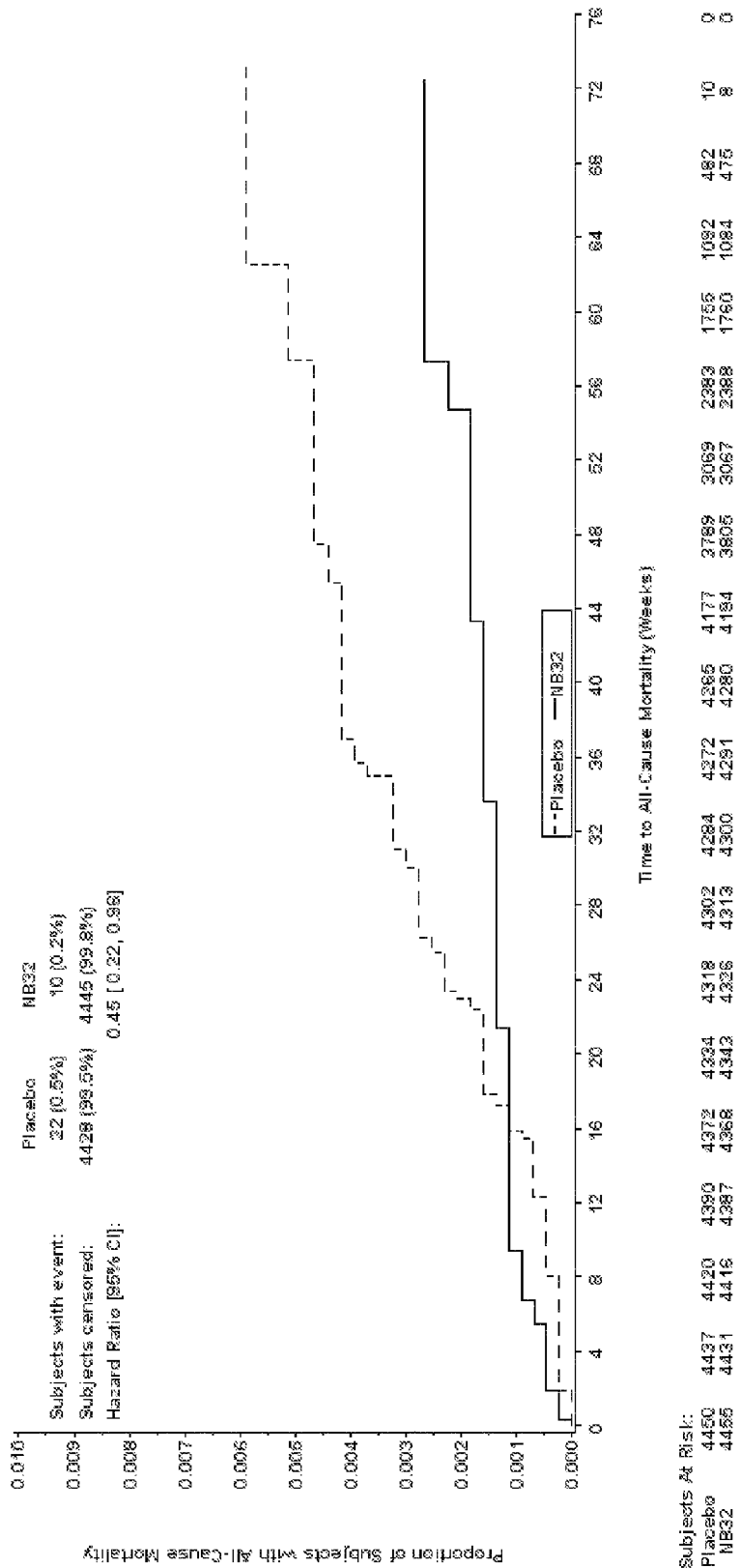

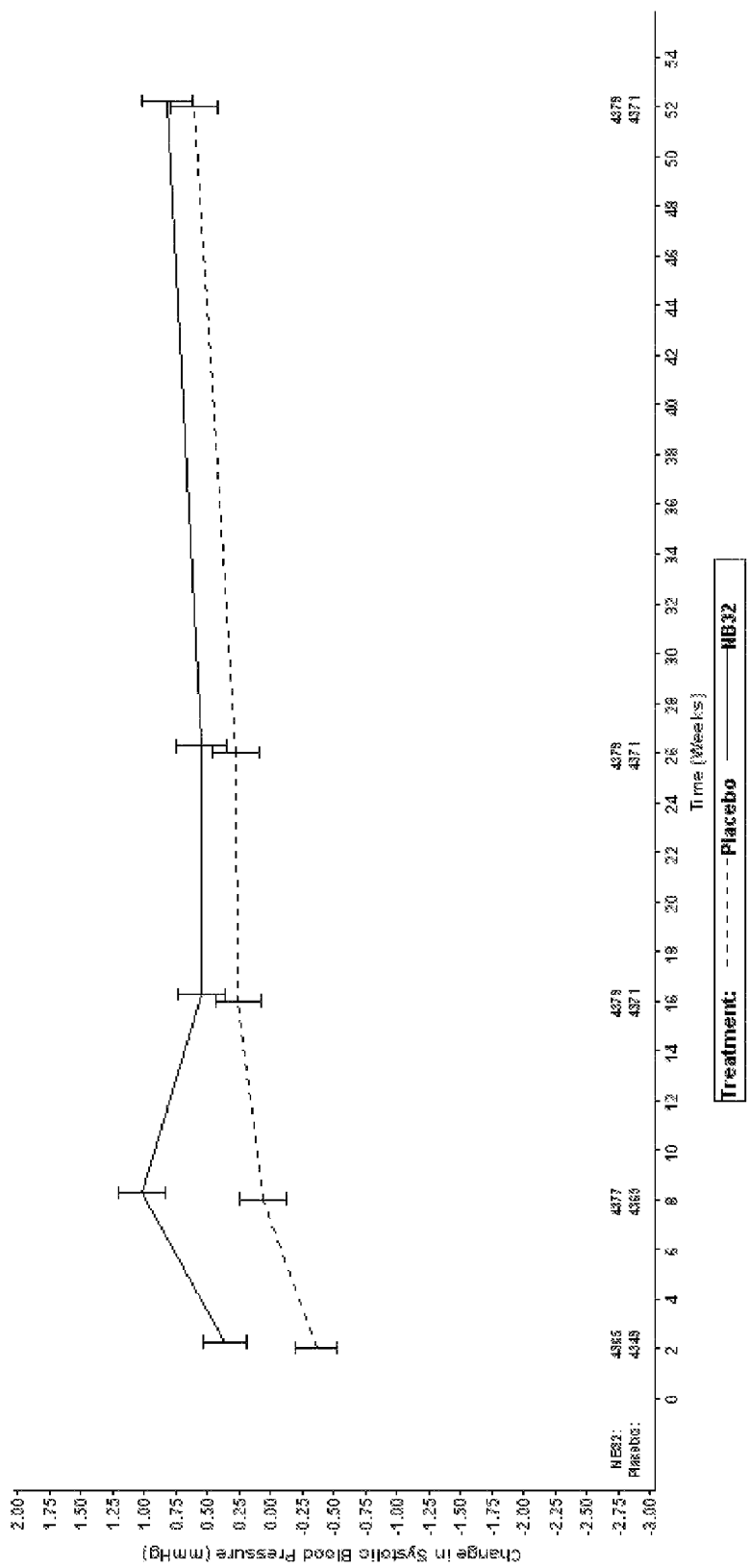

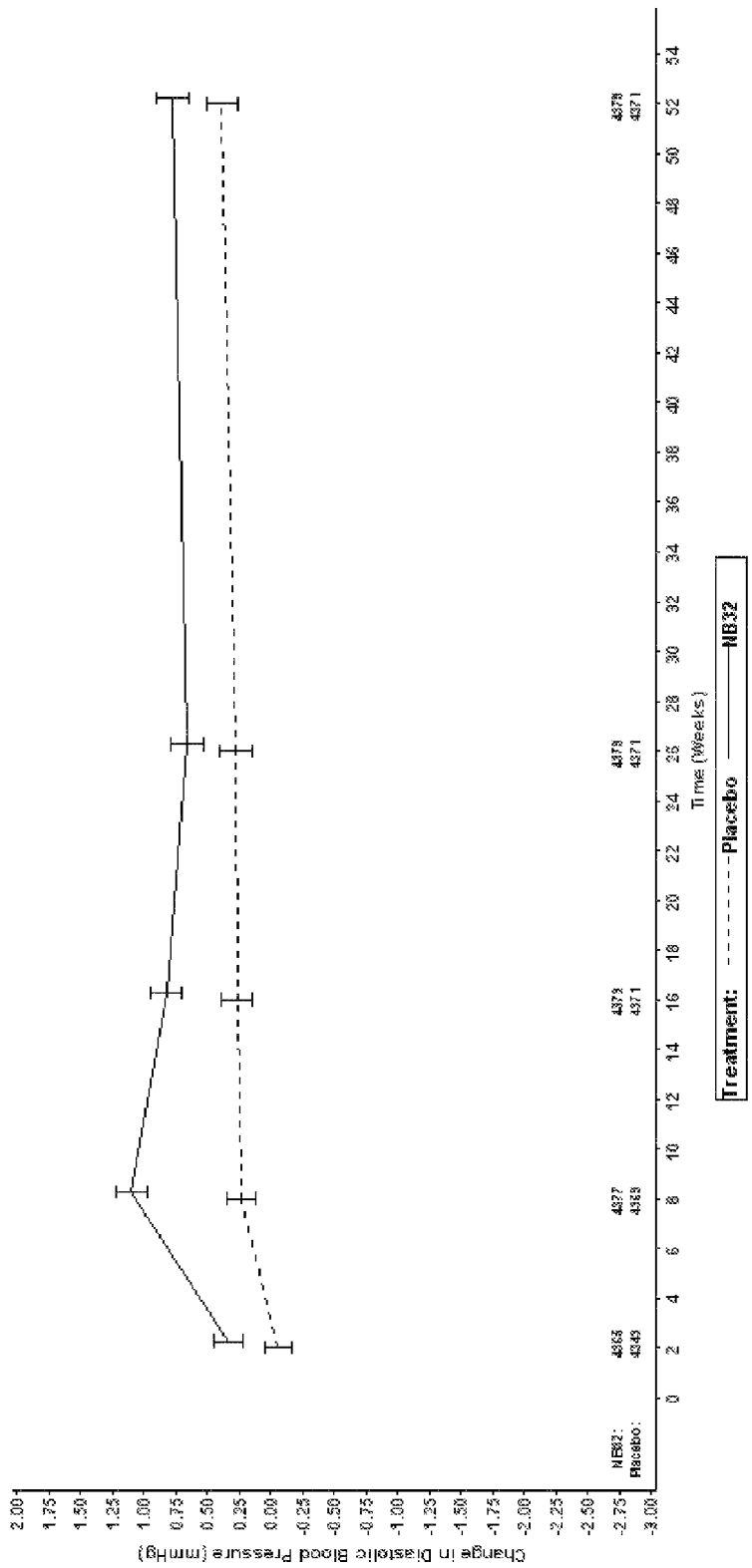

COMPOSITIONS AND METHODS FOR WEIGHT LOSS IN AT RISK PATIENT POPULATIONS

INCORPORATION BY REFERENCE TO RELATED APPLICATIONS

The present application is a continuation of U.S. application Ser. No. 14/322,810, filed Jul. 2, 2014, now U.S. Pat. No. 8,969,371, which claims the benefit of priorities to U.S. Appl. Nos. 61/913,216, filed Dec. 6, 2013; 61/914,938, filed Dec. 11, 2013; and 61/984,580, filed Apr. 25, 2014, each of which is hereby incorporated by references in its entirety. Any and, all priority claims identified in the Application Data Sheet, or any correction thereto, are hereby incorporated by reference under 37 CFR 1.57.

BACKGROUND

The present disclosure relates to compositions, kits, uses, systems and methods for treating overweight and obesity using naltrexone and bupropion, or pharmaceutically acceptable salts thereof. In a preferred embodiment the subject is at increased risk of adverse cardiovascular outcomes, and has type-two diabetes for less than 6 years, or is a current smoker, optionally that does not have type-two diabetes.

Obesity has been defined in terms of body mass index (BMI). BMI is calculated as weight (kg)/[height (m)]$^2$. According to the guidelines of the U.S. Centers for Disease Control and Prevention (CDC) and the World Health Organization (WHO), for adults over 20 years old, BMI is categorized as follows: below 18.5 is considered underweight, 18.5-24.9 is considered normal, 25.0-29.9 is considered overweight, and 30.0 and above is considered obese (World Health Organization. Physical status: The use and interpretation of anthropometry. Geneva, Switzerland: World Health Organization 1995. WHO Technical Report Series).

In most of the anti-obesity drug clinical studies, people with type 1 or 2 diabetes and other serious medical conditions such as increase risk of major adverse cardiovascular events (MACE) are excluded. Major Adverse Cardiovascular Events ("MACEs") include three primary measurements: nonfatal myocardial infarction ("MI"), nonfatal stroke, and cardiovascular death. These major adverse cardiovascular events represent serious ischemic events and are widely used endpoints in cardiovascular outcome trials.

SUMMARY

Some embodiments disclosed herein are related to methods of treating a subject for overweight or obesity, comprising selecting an overweight or obese subject at increased risk of adverse cardiovascular outcomes that has had type-two diabetes for a period of less than 6 years; and treating the subject for overweight or obesity by administering to the subject a daily dose of 32 mg of sustained release naltrexone, or a pharmaceutically acceptable salt thereof and 360 mg bupropion, or a pharmaceutically acceptable salt thereof, for a period of at least 12 weeks.

Some embodiments disclosed herein are related to methods of treating a subject for overweight or obesity, comprising selecting an overweight or obese subject at increased risk of adverse cardiovascular outcomes that is a current smoker that does not have type-two diabetes; and treating the subject for overweight or obesity by administering to the subject a daily dose of 32 mg of sustained release naltrexone and 360 mg bupropion, or a pharmaceutically acceptable salts thereof, for a period of at least 12 weeks.

In some embodiments described herein, the subject was administered about 8 mg of said sustained release naltrexone or a pharmaceutically acceptable salt thereof and about 90 mg of said sustained release bupropion or a pharmaceutically acceptable salt thereof daily for a first week of treatment; about 16 mg of said sustained release naltrexone or a pharmaceutically acceptable salt thereof and about 180 mg of said sustained release bupropion or a pharmaceutically acceptable salt thereof daily for a second week of treatment; about 24 mg of said sustained release naltrexone or a pharmaceutically acceptable salt thereof and about 270 mg of said sustained release bupropion or a pharmaceutically acceptable salt thereof daily for a third week of treatment; and about 32 mg of said sustained release naltrexone or a pharmaceutically acceptable salt thereof and about 360 mg of said sustained release bupropion or a pharmaceutically acceptable salt thereof daily for a fourth week of treatment and any subsequent weeks of treatment.

In some embodiments described herein, the period of treatment is at least 20 weeks.

BRIEF DESCRIPTION OF THE DRAWINGS

FIG. 1 is a graphic depiction of the study design of Examples 1 and 2.

FIG. 2 illustrates the time to first major adverse cardiac event (MACE) for patients receiving naltrexone and bupropion (NB32) or placebo.

FIG. 3 illustrates the percent change in body weight from baseline over time for patients receiving naltrexone and bupropion (NB32) and placebo.

FIG. 4 illustrates the time to cardiovascular death for patients receiving naltrexone and bupropion (NB32) or placebo.

FIG. 5 illustrates the time to first myocardial infarction for patients receiving naltrexone and bupropion (NB32) or placebo.

FIG. 6 illustrates the time to first stroke for patients receiving naltrexone and bupropion (NB32) or placebo.

FIG. 7 illustrates the time to all-cause mortality for patients receiving naltrexone and bupropion (NB32) or placebo.

FIG. 8 illustrates the mean change in systolic blood pressure from baseline over time for patients receiving naltrexone and bupropion (NB32) or placebo.

FIG. 9 illustrates the mean change in diastolic blood pressure from baseline over time for patients receiving naltrexone and bupropion (NB32) or placebo.

DETAILED DESCRIPTION

The combination of naltrexone SR and bupropion SR (Contrave®, NB, or NB32) is being developed by Orexigen Therapeutics, Inc. for treating overweight or obese individuals for weight loss and maintenance of weight loss. To explore the risk of MACE in overweight and obese subjects treated with naltrexone and bupropion, a double-blind, randomized, placebo-controlled study designed to rule out excess cardiovascular (CV) risk in overweight and obese subjects at increased risk of adverse CV outcomes was conducted. This study, described in Example 1, was required by the FDA prior to approval of Contrave because the active ingredients in Contrave, particularly bupropion, were known to increase blood pressure. The FDA was concerned that an increase in blood pressure, while acceptable for the general population, would lead to an unacceptable increase in adverse cardiovascular outcomes in an overweight/obese patient population. Therefore, patients at higher risk of MACE were treated with Contrave or placebo to determine if Contrave led to an unacceptable increase in adverse cardiovascular outcomes.

Example 2 below summarizes some results of this clinical study. Surprisingly, rather than increasing the occurrence of MACE in this high risk patient population, the results indicate that treatment with Naltrexone SR/Bupropion SR (Contrave) decreases the occurrence of MACE in overweight and obese subjects with cardiovascular risk factors. Briefly stated, fewer subjects in the Naltrexone SR/Bupropion SR treatment group experienced a MACE event compared to placebo. In addition, a statistically significant effect on MACE was found for two patient subgroups: patients who have type-2 diabetes for less than 6 weeks, and patients who are current smokers. These subgroups saw a reduction in the risk of MACE that was greater than the general NB patient population tested.

In some embodiments, the subject (e.g., patient or patient population) being treated by the methods disclosed herein is overweight or obese and at increased risk of an adverse cardiovascular event. In some embodiments, the MACE is cardiovascular death, nonfatal myocardial infarction, nonfatal stroke. In some embodiments, the overweight or obese subject at increased risk of adverse CV event or MACE has one or more characteristics or suffers from one or more of: a history of cardiovascular disease (CVD); a current confirmed diagnosis or at high likelihood of CVD; Type 1 diabetes; Type 2 diabetes; dyslipidemia, for example, elevated triglycerides, elevated LDL, or low HDL; hypertension; past or current smoker; a family history of CVD; a genetic predisposition of CVD; unstable angina; cardiac arrhythmia; atrial fibrillation; congestive heart failure; and stroke. In a preferred embodiment, the subject is overweight or obese and at increased risk of a major adverse cardiovascular event, and has Type 2 diabetes mellitus (T2DM) for less than 6 years. In another preferred embodiment, the subject is overweight or obese and at increased risk of a major adverse cardiovascular event, and is a current tobacco smoker. In some embodiments, the current smoker does not have T2DM.

In some embodiments, the overweight or obese subjects that are at increased risk of adverse CV event or MACE include subjects having one or more of the following conditions:

(a) cardiovascular disease (CVD) (confirmed diagnosis or at an increased risk of CVD) optionally with at least one of the following: a history of documented myocardial infarction >3 months prior to screening or identification; a history of coronary revascularization (e.g., coronary artery bypass graft surgery, stent placement, percutaneous transluminal coronary angioplasty, or laser atherectomy); history of carotid or peripheral revascularization (e.g., carotid endarterectomy, lower extremity atherosclerotic disease atherectomy, repair of abdominal aorta aneurysm, femoral or popliteal bypass); angina with ischemic changes (resting ECG), ECG changes on a graded exercise test (GXT), or positive cardiac imaging study; ankle brachial index <0.9 (by simple palpation) within prior 2 years; and ≥50% stenosis of a coronary, carotid, or lower extremity artery within prior 2 years; and/or (b) Type 2 diabetes mellitus, optionally with at least two of the following: hypertension (controlled with or without pharmacotherapy at <145/95 mm Hg); dyslipidemia requiring pharmacotherapy; documented low HDL cholesterol (<50 mg/dL in women or <40 mg/dL in men) within prior 12 months; and current tobacco smoker.

Reduction or decrease of risk is most easily seen when observing a population of treated subjects. Thus, for example, one may observe a decrease in predicted likelihood or risk of MACE in a population by comparing actual MACE in that treated population to a comparable untreated population. As used herein, the same conclusion can be drawn for treatment of an individual or subject falling into an at-risk or enhanced risk category, even if rigid statistical correlations cannot be demonstrated for that case where n=1. Nevertheless, likelihood of MACE for an individual subject is considered to be decreased if it is statistically decreased for any population of subjects to which that individual belongs. References herein to reducing or decreasing likelihood of MACE in a subject should be interpreted to encompass decreasing for an individual subject and/or decreasing the risk for a subject population, unless the context clearly dictates otherwise.

Some embodiments provided herein include methods in which the subject is being treated according to the standard of care with existing medications, including medications to treat diabetes, dyslipidemia, and hypertension. Thus, the embodiments provided herein include administering Naltrexone SR/Bupropion SR to a subject that is at risk of MACE and that is being treated according to the standard of care with a diabetes, dyslipidemia, or hypertension medication. The embodiments provided herein also include administering Naltrexone SR/Bupropion SR to a subject that is taking a diabetes, dyslipidemia, or hypertension medication.

In some embodiments, the administration of naltrexone and bupropion is continued for a period of, or of about, 1, 2, 3, 4, 6, 8, 10, 12, 16, 20, 24, 36, 48, or 52 weeks, or a range defined by any two of the preceding values.

EXAMPLES

The examples below are non-limiting and are merely representative of various aspects of the invention.

Example 1

A Multicenter, Randomized, Double-Blind, Placebo-Controlled Study Assessing the Occurrence of Major Adverse Cardiovascular Events (MACE) in Overweight and Obese Subjects With Cardiovascular Risk Factors Receiving 32 mg Naltrexone SR/360 mg Bupropion SR ("NB" or "NB32"). The study consists of three periods (see FIG. 1):

1) Screening Period (starting at Visit 1, Screen, with informed consent): up to 2 weeks to verify eligibility prior to the first dose of study medication in the lead-in period.

2) Lead-in Period (starting at Visit 2, Week-2): double-blind, 2-week period during which the subjects receive treatment according to one of two sequences: 1 week of active study medication (8 mg naltrexone SR/90 mg bupropion SR [NB32]) once a day followed by 1 week of placebo once a day; or 1 week of placebo followed by 1 week of active study medication. Subjects are randomly assigned to NB32 or placebo for the lead-in period.

3) Treatment Period (starting at Visit 3, Day 1): double-blind, randomized period during which the subjects who completed the lead-in period and satisfied inclusion/exclusion criteria receive active study medication or placebo. The treatment period starts upon randomization at Visit 3 (Day 1).

a) At Visit 6 (Week 16) there is an evaluation of weight loss and blood pressure changes relative to baseline observations. The target weight loss is ≥5% with expected minimum weight loss at 16 weeks of ≥2%. Subjects should be discontinued from study medication at Week 16 if:

they have not lost at least 2% of their body weight or they are experiencing sustained (e.g., at 2 or more visits) increases in blood pressure (systolic or diastolic) of ≥10 mm Hg. If the Investigator suspects that an elevated blood pressure measurement may be spurious, subjects should not be discontinued until the elevated measurement is confirmed within 4 weeks.

b) All subjects participate in a comprehensive web-based weight management program through completion of study procedures, regardless of whether they are taking study medication.

c) Every other month between visits past Visit 7 (Week 26), subjects are asked to answer specific questions pertaining to compliance and hospitalizations (potential MACE or serious adverse events [SAEs]), using an internet- or telephone-based data collection system.

d) All randomized subjects who discontinue study medication early complete the End-of-Treatment Visit procedures and continue to participate in the study for the remainder of the trial for collection of MACE data. Subjects are asked to come to the study site at their scheduled visits and complete the internet- or telephone-based data collection every other month between visits past Visit 7 (Week 26) even though they are no longer taking study medication.

Subjects must meet all of the following inclusion criteria to be eligible for participation in this study.

1. ≥50 years of age (women) or ≥45 years of age (men)
2. Body mass index (BMI)≥27 kg/m2 and ≤50 kg/m2
3. Waist circumference ≥88 cm (women) or ≥102 cm (men)
4. At increased risk of adverse cardiovascular outcomes:
   a. Cardiovascular disease (confirmed diagnosis or at high likelihood of cardiovascular disease) with at least one of the following:
      History of documented myocardial infarction >3 months prior to screening
      History of coronary revascularization (i.e., coronary artery bypass graft surgery, stent placement, percutaneous transluminal coronary angioplasty, or laser atherectomy)
      History of carotid or peripheral revascularization (i.e., carotid endarterectomy, lower extremity atherosclerotic disease atherectomy, repair of abdominal aorta aneurysm, femoral or popliteal bypass)
      Angina with ischemic changes (resting ECG), ECG changes on a graded exercise test (GXT), or positive cardiac imaging study
      Ankle brachial index <0.9 (by simple palpation) within prior 2 years
      ≥50% stenosis of a coronary, carotid, or lower extremity artery within prior 2 years
      and/or
   b. Type 2 diabetes mellitus with at least 2 of the following:
      Hypertension (controlled with or without pharmacotherapy at <145/95 mm Hg)
      Dyslipidemia requiring pharmacotherapy
      Documented low HDL cholesterol (<50 mg/dL in women or <40 mg/dL in men) within prior 12 months
      Current tobacco smoker.

Subjects having the following characteristics are to be excluded: Myocardial infarction within 3 months prior to screening; Angina pectoris Grade III or IV as per the Canadian Cardiovascular Society grading scheme; Clinical history of cerebrovascular disease (stroke); History of tachyarrhythmia other than sinus tachycardia; Blood pressure ≥145/95 mm Hg, irrespective of treatment with antihypertensive agents; Unstable weight within 3 months prior to screening (e.g., weight gain or loss of >3%); Planned bariatric surgery, cardiac surgery, or coronary angioplasty; Severe renal impairment defined by an estimated GFR <30 mL/min; Clinical history of liver failure or documented ALT or AST greater than 3 times the upper limit of normal (ULN); Known infection with HIV or hepatitis; Chronic use or positive screen for opioids; Recent drug or alcohol abuse or dependence (with the exception of nicotine dependence) within 6 months prior to screening; History of seizures (including febrile seizures), cranial trauma, or other conditions that predispose the subject to seizures; History of mania or current diagnosis of active psychosis, active bulimia or anorexia nervosa (binge eating disorder is not exclusionary); At risk for suicide attempts based on the judgment of the Investigator; Acute depressive illness including new onset of depression or acute exacerbation of symptoms (stable subjects on chronic treatment for depression are not excluded); Any condition with life expectancy anticipated to be less than 4 years (e.g., congestive heart failure NYHA Class 3 or 4); History of malignancy within the previous 5 years, with exception of non-melanoma skin cancer or surgically cured cervical cancer; Current use of other bupropion or naltrexone containing products; History of hypersensitivity or intolerance to naltrexone or bupropion; Use of monoamine oxidase inhibitors within 14 days prior to screening; Use of any investigational drug, device, or procedure within 30 days prior to screening; Pregnant or breast-feeding women, or currently trying to become pregnant, or of child-bearing potential (including peri-menopausal women who have had a menstrual period within one year) and not willing to practice birth control; Inability to consistently access broadband internet; Employment by the Sponsor or the study site, or co-habitation with another individual enrolled in the study.

The study medication (NB and placebo) is provided as tablets. Each active tablet contains 8 mg naltrexone SR/90 mg bupropion SR (8/90). All tablets, including placebo, are identical in appearance to maintain blinding. Dose escalation occurs during the first 4 weeks of the treatment period, as shown in the Table 1 below. Doses can be taken with or without food.

TABLE 1

| | Lead-in Period | | Treatment Period | | | |
|---|---|---|---|---|---|---|
| Dose Schedule | Week-2 | Week-1 | Week 1 (Days 1-7) | Week 2 (Days 8-14) | Week 3 (Days 15-21) | Week 4 through end of study |
| Total Daily Dose* | 8/90 NB | 8/90 NB | 8/90 NB | 16/180 NB | 24/270 NB | 32/360 NB |
| Morning | 1 tab NB or PBO | 1 tab PBO or NB | 1 tab NB or PBO | 1 tab NB or PBO | 2 tabs NB or PBO | 2 tabs NB or PBO |
| Evening | — | — | — | 1 tab NB or PBO | 1 tab NB or PBO | 2 tabs NB or PBO |

*Doses shown are of naltrexone SR/bupropion SR (NB):
tab = tablet;
PBO = placebo.

Example 2

Example 2 summarizes Contrave cardiovascular outcome clinical study (NB-CVOT) results demonstrating that treatment with 32 mg naltrexone sustained-release (SR)/360 mg bupropion SR (NB or NB32) does not increase or decreases the occurrence of Major Adverse Cardiovascular Events (MACE) in overweight and obese subjects with cardiovascular risk factors. The general study patient inclusion criteria and protocol are described in the Example 1. The treatment period is ongoing, and the results reported are interim results.

At Week 16, there was an evaluation of weight loss and blood pressure changes relative to baseline observations. Subjects were to be discontinued from study medication at Week 16 if they had not lost at least 2% of their body weight or they were experiencing consecutive, sustained increases in blood pressure (systolic or diastolic) of ≥10 mm Hg.

Study drug is to be administered, double-blind, for 3 to 4 years (2 weeks lead-in period and 3 to 4 years treatment period). At the time of the interim analysis, mean duration of exposure to study drug was 26.84 weeks for the placebo group and 30.47 weeks for the NB group. Total subject-years on study medication for the placebo and NB groups were 2289 and 2602, respectively.

Overall, 13,192 subjects were screened for eligibility, of which 10,504 were enrolled into the lead-in period. A total of 8910 subjects who completed the lead-in period were subsequently randomized into the treatment period and received at least one dose of treatment period study medication (4450 to placebo and 4454 to NB). As of the 6 Nov. 2013 data cutoff for the interim analysis, 1201 (placebo) and 1708 (NB) subjects were continuing treatment with study medication. The majority of the subjects in the ITT Population (95.2%) continued to be followed for MACE while 4.8% were classified as non-retainable for MACE follow-up because they revoked their consent or became lost to follow-up. Importantly, vital status checks using public records were performed for all subjects who were classified as non-retainable for MACE follow-up. Of the 428 subjects who were classified as non-retainable for MACE follow-up, vital status was obtained for 359 subjects leaving 69 subjects (0.8% of the ITT Population) with no vital status (either not obtained or pending) at the time of this interim analysis. The most common reason for discontinuation of study medication during the treatment period for NB was due to an AE (7.4% placebo, 26.7% NB) and for placebo was not meeting Week 16 continuation of treatment criteria (40.7% placebo, 14.2% NB). All other reasons for discontinuation of study medication were balanced between treatment groups.

Demographic and Baseline Body Mass Characteristics

Demographic and baseline characteristics for subjects in the ITT Population follows. The majority of subjects were female (54.5%), White (83.5%), and not Hispanic or Latino (93.5%). Mean age was 61.0 years. Mean baseline body weight (106.0 kg), BMI (37.3 kg/m$^2$), and waist circumference (119.5 cm) were consistent with the criteria for overweight and obese.

The majority of subjects had T2DM (85.2%) with a smaller proportion having a history of CV disease (CVD, 32.1%). Treatment assignment was balanced within the primary baseline risk groups with an overall distribution of 67.8%, 14.8%, and 17.3% for T2DM only, CVD only, or T2DM with CVD, respectively.

Among subjects with T2DM, the median duration of T2DM was 7.7 years with 58.9% reporting durations of ≥6 years. Mean baseline HbA1c was 7.4%, and 52.7% had an HbA1c ≥7%. Antidiabetic medication use at baseline was 78.7% among all subjects in the ITT Population, which reflected primarily metformin use (63.9%). Subjects with T2DM were not required to have an HbA1c value within a specified range for inclusion in the study and there were no restrictions on antidiabetic medications.

The incidence of subjects with hypertension at baseline was 92.9%. Antihypertension medication use at baseline was 93.4%, which reflected primarily angiotensin-converting enzyme inhibitors (ACEI)/angiotensin II receptor blocker (ARB) use (78.0%). Similarly, 91.8% of the subjects reported dyslipidemia at baseline. Lipid altering medication use at baseline was 88.4%, which was mostly attributed to statin (HMG-CoA reductase inhibitor) use (80.4%). The incidence of subjects who were current tobacco smokers at screening was 9.2% and comparable between treatment groups. The CV related baseline conditions, including laboratory values and associated medication use, were comparable between treatment groups and indicate that the subjects, while exhibiting increased CV risk, were also treated for associated comorbidities according to standard of care.

Demographics and baseline characteristics were balanced between treatment groups. There were no unexpected differences in the incidences and pattern of demographic and baseline characteristics among the CV risk groups.

Medical History

To qualify for entry into the study, subjects were to be at increased risk of CV outcomes by either having CV disease, T2DM, or both as defined in inclusion criterion 4 of the protocol set forth in Example 1. To be included in the CV disease risk group "CV disease," subjects were to have at least one of the following: history of MI>3 months prior to screening (13.3%); coronary, carotid or peripheral revascularization (25.9%, 0.9%, and 0.7%, respectively); angina with ischemic changes, ECG changes on a graded exercise test, or positive cardiac imaging study (3.8%); ankle brachial index <0.9 within prior 2 years (0.6%); or ≥50% stenosis of a coronary, carotid, or lower extremity artery within prior 2 years (3.6%, 0.7%, and 0.2%, respectively).

To be included in the CV disease risk group "T2DM," subjects were to have T2DM (85.2%) with at least two of the following: history of hypertension (92.9%), dyslipidemia requiring pharmacotherapy (91.8%), documented low HDL within the prior 12 months (29.4%), or was a current smoker (9.2%).

CV medical history was balanced between treatment groups. The incidences and pattern of CV medical history for each CV risk group were expected for a population with CV disease, T2DM, or both.

Analyses of Body Weight and Blood Pressure

Overall, mean weight loss was consistently 2% to 3% greater for NB than placebo (FIG. 3). The clinically and statistically meaningful weight loss was further demonstrated by the higher proportion of subjects achieving ≥10% weight loss from baseline to Week 52 with NB (12.3%) compared to placebo (3.3%); odds ratio 4.13 (p<0.0001). The weight loss observed in this study is consistent with weight loss in subjects with T2DM in previous NB studies, but the absolute and placebo-corrected weight loss is less than observed for the non-diabetic population in previous studies with NB.

In the NB group, blood pressure values were approximately 0.5 mm Hg higher than placebo at most time points, which peaked at Week 8 with a treatment difference of approximately 1 mm Hg that resolved by Week 16.

Primary MACE Analysis

The incidence of first MACE for the ITT Population is presented in Table 2. The total subject-years at risk was similar between the treatment groups. The background MACE rate was 1.3% (placebo group), consistent with the intended target of enrolling subjects with a background MACE rate of 1-1.5%.

Fewer subjects treated with NB (35, 0.8%) experienced a primary endpoint event compared to placebo (59, 1.3%); HR (hazard ratio) (95% CI) 0.59 (0.39-0.90). The incidence of the individual MACE components of CV death and nonfatal MI was lower for the NB group than placebo, and the incidence of the MACE component nonfatal stroke was similar between groups.

These results clearly meet the pre-specified requirement set forth by the FDA of excluding a HR of 2.0 (a doubling of the risk). Furthermore, the favorable point estimate and upper bound of the 95% CI of less than 1.0 indicate that the risk of MACE with NB is not elevated compared to placebo. A HR of less than 1.0 indicates that NB reduces the risk of MACE.

Separation of the primary endpoint results by treatment occurred early and was favorable for NB throughout the assessment period (FIG. 2).

TABLE 2

Incidence of First MACE: ITT Population

|  | Placebo (N = 4450) | NB (N = 4455) |
|---|---|---|
| MACE, n (%) of Subjects | 59 (1.3%) | 35 (0.8%) |
| CV Death | 16 (0.4%) | 5 (0.1%) |
| Nonfatal MI | 33 (0.7%) | 23 (0.5%) |
| Nonfatal Stroke | 10 (0.2%) | 7 (0.2%) |
| Total Subject-years at Risk | 4757.7 | 4769.0 |
| HR (95% CI)[1] |  | 0.59 (0.39, 0.90) |
| p-value[2] |  | <0.0001 |

Abbreviations:
CI = confidence interval;
CV = cardiovascular;
HR = hazard ratio;
MACE = major adverse cardiovascular events;
MI = myocardial infarction;
NB = naltrexone SR 32 mg/bupropion SR 360 mg.
[1]Based on Cox proportional hazards model with treatment as a factor.
[2]p-value for testing the null hypothesis of HR ≥ 2 vs. one-sided alternative.

Primary MACE Subgroup Analyses

The primary outcome variable (time to first MACE) was evaluated by the following demographic variables and baseline characteristics: CV risk group, age category, sex, race grouping, ethnicity, BMI category, smoking status, HbA1c category, study medication class, duration of T2DM category, and renal impairment category. These analyses were conducted to explore potential variation in the treatment effect.

Of the subgroups analyzed, two subgroups showed statistically significant differences in time to first MACE: smoking status and duration of T2DM. The HRs for the incidence of first MACE for these subgroups are presented in Table 3 for the ITT Population. The risk for MACE with NB relative to placebo by subgroup was generally similar for the PP Population.

TABLE 3

Incidence of First MACE by Subgroup: ITT Population

| Subgroup | Treatment | N | n (%) | HR (95% CI)[1] |
|---|---|---|---|---|
| Smoking Status p = 0.0241[2] | | | | |
| No | Placebo | 4036 | 49 (1.2%) | |
|  | NB | 4050 | 34 (0.8%) | 0.69 (0.44, 1.07) |
| Yes | Placebo | 414 | 10 (2.4%) | |
|  | NB | 405 | 1 (0.2%) | 0.10 (0.01, 0.77) |

TABLE 3-continued

Incidence of First MACE by Subgroup: ITT Population

| Subgroup | Treatment | N | n (%) | HR (95% CI)[1] |
|---|---|---|---|---|
| Duration of T2DM Category p = 0.0182[2] | | | | |
| <6 years | Placebo | 1561 | 18 (1.2%) | |
|  | NB | 1494 | 4 (0.3%) | 0.24 (0.08, 0.70) |
| ≥6 years | Placebo | 2166 | 25 (1.2%) | |
|  | NB | 2205 | 24 (1.1%) | 0.93 (0.53, 1.64) |

Abbreviations:
CI = confidence interval;
NB = naltrexone SR 32 mg/bupropion SR 360 mg;
T2DM = type 2 diabetes mellitus.
[1]Based on Cox proportional hazards model; factors and covariates used to calculate the HR and 95% CI for each subgroup are summarized in the source tables.
[2]Likelihood ratio-test for comparing the model with treatment*subgroup interaction term and without interaction term.

These results show that subjects that have T2DM less than 6 years have a HR of 0.24, whereas those with T2DM 6 or more years have a HR of 0.93. In comparison, the HR for the entire study population was 0.59. Patients with T2DM less than 6 years treated with NB have a significantly reduced risk of MACE compared to those with T2DM 6 or more years. Similarly, subjects that are current smokers have a HR of 0.10, whereas non-smokers have a HR of 0.69. Current smokers treated with NB have a significantly reduced risk of MACE compared to non-smokers.

Time to Cardiovascular Death

The CV death endpoint includes adjudicated outcomes of sudden cardiac death, fatal MI, fatal stroke, and other fatal CV causes. The incidence of CV death for the ITT Population are presented in Table 4. The HR (95% CI) was 0.26 (0.10, 0.70) and 0.56 (0.16, 1.94) for the ITT and PP Populations, respectively, indicating that an excess risk of CV death has been excluded at the time of the analysis. Sudden cardiac death and other fatal CV causes were the primary contributors to the endpoint. Separation of the CV death endpoint results by treatment for the ITT and PP Populations occurred by Week 20 and was favorable for NB for the remainder of the assessment period (FIG. 4).

TABLE 4

Incidence of Cardiovascular Death

| | ITT Population | |
|---|---|---|
|  | Placebo (N = 4450) | NB (N = 4455) |
| CV Death, n (%) of Subjects | 19 (0.4%) | 5 (0.1%) |
| Sudden Cardiac Death | 8 (0.2%) | 3 (<0.1%) |
| Fatal MI | 3 (<0.1%) | 1 (<0.1%) |
| Fatal Stroke | 1 (<0.1%) | 0 |
| Other Fatal CV Causes | 7 (0.2%) | 1 (<0.1%) |
| Total Subject-years at Risk | 4782.3 | 4787.5 |
| HR (95% CI)[1] |  | 0.26 (0.10, 0.70) |
| p-value[2] |  | <0.0001 |

Abbreviations:
CI = confidence interval;
CV = cardiovascular;
HR = hazard ratio;
MI = myocardial infarction;
NB = naltrexone SR 32 mg/bupropion SR 360 mg.
[1]Based on Cox proportional hazards model with treatment as a factor.
[2]p-value for testing the null hypothesis of HR ≥ 2 vs. one-sided alternative.

Time to First Myocardial Infarction

The MI endpoint includes adjudicated outcomes of fatal and nonfatal MI. The incidence of first MI for the ITT Population is presented in Table 5. The HR (95% CI) was 0.70

(0.42, 1.19) and 0.83 (0.40, 1.71) for the ITT and PP Populations, respectively, indicating that an excess risk of MI has been excluded at the time of the analysis. Throughout the study, the risk of MI with NB was either favorable or similar to placebo for the ITT and PP Populations (FIG. 5).

TABLE 5

Incidence of First Myocardial Infarction

|  | ITT Population | |
| --- | --- | --- |
|  | Placebo (N = 4450) | NB (N = 4455) |
| MI, n (%) of Subjects | 34 (0.8%) | 24 (0.5%) |
| Nonfatal MI | 33 (0.7%) | 23 (0.5%) |
| Fatal MI | 1 (<0.1%) | 1 (<0.1%) |
| Total Subject-years at Risk | 4763.1 | 4773.2 |
| HR (95% CI)[1] |  | 0.70 (0.42, 1.19) |
| p-value[2] |  | <0.0001 |

Abbreviations:
CI = confidence interval;
HR = hazard ratio;
MI = myocardial infarction;
NB = naltrexone SR 32 mg/bupropion SR 360 mg.
[1]Based on Cox proportional hazards model with treatment as a factor.
[2]p-value for testing the null hypothesis of HR ≥ 2 vs. one-sided alternative.

Time to First Stroke

The stroke endpoint includes adjudicated outcomes of fatal and nonfatal stroke. The incidence of first stroke for the ITT Population is presented in Table 6. The HR (95% CI) was 0.63 (0.25, 1.64) for the ITT Population, indicating that an excess risk of stroke has been excluded at the time of the analysis for this population.

Separation of the stroke endpoint results by treatment for the ITT Population occurred after Week 20 and was favorable for NB for the remainder of the assessment period (FIG. 6); the proportion of subjects with stroke in the PP Population was generally similar between treatment groups throughout the study.

TABLE 6

Incidence of First Stroke

|  | ITT Population | |
| --- | --- | --- |
|  | Placebo (N = 4450) | NB (N = 4455) |
| Stroke, n (%) of Subjects | 11 (0.2%) | 7 (0.2%) |
| Nonfatal Stroke | 10 (0.2%) | 7 (0.2%) |
| Fatal Stroke | 1 (<0.1%) | 0 |
| Total Subject-years at Risk | 4777.0 | 4783.3 |
| HR (95% CI)[1] |  | 0.63 (0.25, 1.64) |
| p-value[2] |  | 0.0088 |

Abbreviations:
CI = confidence interval;
HR = hazard ratio;
NB = naltrexone SR 32 mg/bupropion SR 360 mg.
[1]Based on Cox proportional hazards model with treatment as a factor.
[2]p-value for testing the null hypothesis of HR ≥ 2 vs. one-sided alternative.

All-Cause Mortality Endpoint and Other Cardiovascular Endpoints

An overview of the all-cause mortality endpoint and other CV endpoint measures for the ITT Population is presented in Table 7. The HR (95% CI) for all-cause mortality had a point estimate favoring NB (0.45 [0.22, 0.96]). As expected given the population and study design, CV death was the primary contributor to the all-cause mortality endpoint. Separation of the all-cause mortality endpoint results by treatment for the ITT Population occurred after Week 16 and was favorable for NB for the remainder of the assessment period (FIG. 7). More subjects treated with NB experienced an endpoint event of HUSA (29, 0.7%) compared to placebo (23, 0.5%); HR (95% CI) 1.26 (0.73, 2.18). Separation of HUSA endpoint results by treatment for the ITT Population occurred early and was favorable for placebo. Importantly, this observation was not associated with an increase in coronary revascularization events (HR [95% CI] of 1.00 [0.71, 1.41]). An endpoint event of coronary revascularization procedures was experienced by 65 (1.5%) subjects in each treatment group. Throughout the study, the risk of coronary revascularization events with NB was similar to placebo for the ITT Population.

The HR (95% CI) for first five-point expanded MACE had a point estimate favoring NB (0.87 [0.65, 1.15]). Five-point expanded MACE includes adjudicated outcomes of CV death, nonfatal MI, nonfatal stroke, nonfatal HUSA, and coronary revascularization procedure. The incidence of first coronary revascularization procedure, the only term not included for four-point expanded MACE, was similar for both treatment groups (0.7% each). The all-cause mortality endpoint and other CV endpoint measures were also evaluated for the ITT Population by CV risk group, age category, sex, race grouping, ethnicity, and BMI category.

TABLE 7

Incidence of All-Cause Mortality Endpoint and Other Cardiovascular Endpoints

|  | ITT Population | |
| --- | --- | --- |
|  | Placebo (N = 4450) | NB (N = 4455) |
| All-Cause Mortality, n (%) of Subjects | 22 (0.5%) | 10 (0.2%) |
| CV Death | 19 (0.4%) | 5 (0.1%) |
| Non-CV Death | 3 (<0.1%) | 5 (0.1%) |
| Total Subject-years at Risk | 4782.3 | 4787.5 |
| HR (95% CI)[1] |  | 0.45 (0.22, 0.96) |
| p-value[2] |  | <0.0001 |

Abbreviations:
CI = confidence interval;
CV = cardiovascular;
HR = hazard ratio;
NB = naltrexone SR 32 mg/bupropion SR 360 mg.
[1]Based on Cox proportional hazards model with treatment as a factor.
[2]p-value for testing the null hypothesis of HR ≥ 2 vs. one-sided alternative.

Change in Systolic Blood Pressure

The mean change in systolic blood pressure from baseline by visit for the ITT (with LOCF) Population is presented in FIG. 8. Note that only 44.8% of subjects had completed the Week 52 visit prior to the interim analysis cut-off date. Thus, the last observation taken at the time of the cut-off date was carried forward to Week 52 for subjects receiving medication who had not yet reached Week 52. Blood pressure changes were slightly more favorable with placebo than NB at each time point. In the placebo group, mean systolic blood pressure decreased below baseline at Week 2, then steadily increased through Week 52. In the NB group, systolic blood pressure values were approximately 0.5 mm Hg higher than placebo at most time points, which peaked at Week 8 with a treatment difference of approximately 1 mm Hg that resolved by Week 16.

Subjects who did not meet the continuation of treatment criteria due to sustained increases in blood pressure (or insufficient weight loss) were discontinued from treatment, which is reflected in a sharp decrease in the systolic blood pressure after Week 16 for both treatment groups for the PP Population compared to the ITT Population (with LOCF). Additionally, all subjects in the NB group were on treatment at each time point per the PP Population definition and under the sympathomimetic effects of bupropion, which contributed to the magnitude of the treatment difference after Week 16 compared to the ITT Population (with LOCF).

Change in Diastolic Blood Pressure

The mean change in diastolic blood pressure from baseline by visit for the ITT (with LOCF) Population is presented in FIG. 9. Note that only 44.8% of subjects had completed the Week 52 visit prior to the interim analysis cut-off date. Thus, the last observation taken at the time of the cut-off date was carried forward to Week 52 for subjects receiving medication who had not yet reached Week 52. Blood pressure changes were more favorable with placebo than NB at each time point. In the placebo group, mean diastolic blood pressure was within 1 mm Hg from baseline at each time point through Week 52. In the NB group, diastolic blood pressure values were approximately 0.5 mm Hg higher than placebo at most time points, which peaked at Week 8 with a treatment difference of approximately 1 mm Hg that resolved by Week 16.

Subjects who did not meet the continuation of treatment criteria due to sustained increases in blood pressure (or insufficient weight loss) were discontinued from treatment, which is reflected in a sharp decrease in the diastolic blood pressure after Week 16 for both treatment groups for the PP Population compared to the ITT Population (with LOCF). Additionally, all subjects in the NB group were on treatment at each time point per the PP Population definition and under the sympathomimetic effects of bupropion, which contributed to the magnitude of the treatment difference after Week 16 compared to the ITT Population (with LOCF).

Overall, the small relative increases in diastolic blood pressure with NB treatment relative to placebo in NB-CVOT are consistent with that observed in the Phase 3 program.

CONCLUSIONS

In conclusion, the favorable point estimate for the hazard ratio (HR) and upper bound of the 95% CI of less than 1.0 at the time of this interim analysis indicate that the risk of MACE in overweight and obese subjects treated with NB is not increased compared to those receiving placebo. The point estimate for primary MACE observed in this study (HR [95% CI]: 0.59 [0.39, 0.90]) suggests that the treatment with NB reduces the risk of MACE, rather than increasing it as anticipated by the FDA. Of note, these favorable results were observed in a population well treated according to standard of care with medications to treat diabetes, dyslipidemia, and hypertension. Despite the small relative increases in blood pressure with NB treatment, which were also observed in earlier trials, the results of the MACE endpoints at the time of the interim analysis clearly suggests no harm related to the mild sympathomimetic action of NB.

While the patient population receiving NB had a reduced HR for MACE, two NB patient subpopulations demonstrated a statistically significant effect on the risk of MACE: smoking status and duration of T2DM. Current smokers (HR [95% CI]: 0.10 [0.01, 0.77]) and patients with T2DM less than 6 years (HR [95% CI]:0.24 [0.08, 0.70]) showed a greater reduction in the risk of MACE compared to non-smokers (HR [95% CI]: 0.69 [0.44, 1.07]) and patients with T2DM 6 or more years (HR [95% CI]: 0.93 (0.53, 1.64]). Based on these results, overweight or obese patients at increased risk of adverse cardiovascular events who are current smokers or have T2DM less than 6 years will benefit from treatment with NB by significantly reducing their risk of MACE compared to the general population of overweight or obese patients at increased risk of adverse cardiovascular events.

What is claimed is:

1. A method of treating a subject for overweight or obesity, comprising:
    selecting for treatment an overweight or obese subject at increased risk of a major adverse cardiovascular event that (a) has had type-two diabetes for a period of less than 6 years, or (b) is a current smoker that does not have type-two diabetes; and
    treating the subject for overweight or obesity by administering to the subject a daily dose of 32 mg of sustained release naltrexone, or a pharmaceutically acceptable salt thereof and 360 mg bupropion, or a pharmaceutically acceptable salt thereof, for a period of at least 12 weeks, wherein said administering reduces the risk of a major adverse cardiovascular event in said overweight or obese subject.

2. The method of claim 1, wherein the subject was administered:
    about 8 mg of said sustained release naltrexone or a pharmaceutically acceptable salt thereof and about 90 mg of said sustained release bupropion or a pharmaceutically acceptable salt thereof daily for a first week of treatment;
    about 16 mg of said sustained release naltrexone or a pharmaceutically acceptable salt thereof and about 180 mg of said sustained release bupropion or a pharmaceutically acceptable salt thereof daily for a second week of treatment;
    about 24 mg of said sustained release naltrexone or a pharmaceutically acceptable salt thereof and about 270 mg of said sustained release bupropion or a pharmaceutically acceptable salt thereof daily for a third week of treatment; and
    about 32 mg of said sustained release naltrexone or a pharmaceutically acceptable salt thereof and about 360 mg of said sustained release bupropion or a pharmaceutically acceptable salt thereof daily for a fourth week of treatment and any subsequent weeks of treatment.

3. The method of claim 1, wherein the period of treatment is at least 20 weeks.

* * * * *